(12) United States Patent
Rothman

(10) Patent No.: US 7,426,852 B1
(45) Date of Patent: *Sep. 23, 2008

(54) SUBMERSIBLE METER FOR MEASURING A PARAMETER OF GAS HOLD-UP OF A FLUID

(75) Inventor: Paul Rothman, Windsor, CT (US)

(73) Assignee: Expro Meters, Inc., Wallingford, CT (US)

( * ) Notice: Subject to any disclaimer, the term of this patent is extended or adjusted under 35 U.S.C. 154(b) by 7 days.

This patent is subject to a terminal disclaimer.

(21) Appl. No.: 11/115,492

(22) Filed: Apr. 26, 2005

Related U.S. Application Data

(60) Provisional application No. 60/634,326, filed on Dec. 7, 2004, provisional application No. 60/587,610, filed on Jul. 12, 2004, provisional application No. 60/565,357, filed on Apr. 26, 2004.

(51) Int. Cl.
*G01N 29/24* (2006.01)
(52) U.S. Cl. .................. 73/61.49; 73/61.79; 73/597; 702/54; 702/56
(58) Field of Classification Search ........... 73/597–600, 73/61.79, 19.03, 61.47, 61.49; 702/45, 47, 702/50, 54, 56, 100, 103
See application file for complete search history.

(56) References Cited

U.S. PATENT DOCUMENTS

| | | | |
|---|---|---|---|
| 2,874,568 A | 2/1959 | Petermann | |
| 3,715,709 A | 2/1973 | Zacharies et al. | |
| 3,751,979 A | 8/1973 | Ims | 73/861.27 |
| 3,851,521 A | 12/1974 | Ottenstein | 73/40.5 |
| 3,885,432 A | 5/1975 | Herzl | 73/861.22 |

(Continued)

FOREIGN PATENT DOCUMENTS

GB 1578660 A * 11/1980

(Continued)

OTHER PUBLICATIONS

Kellerman et al, "Dynamic modelling of gas hold-up in different electrolyte systems", 1998, Chapman and Hall, pp. 311-319.*

(Continued)

*Primary Examiner*—Hezron E. Williams
*Assistant Examiner*—Nashmiya S Fayyaz

(57) ABSTRACT

A submersible meter is provided that measures the speed of sound propagating in an aerated fluid to determine any one of a plurality of parameters of the fluid, such as the gas holdup of the fluid ($\epsilon_b$), the bubble size ($d_b$), the bubble surface area flux ($S_b$), and the flotation rate constant (k). The meter includes a spatial array of sensors disposed at predetermined axial locations $x_1$-$x_N$ axially along a tube. The array of sensors provide acoustic pressure signals $P_1(t)$-$P_N(t)$ to a transmitter which determines the speed of sound $a_{mix}$ propagating through the aerated fluid in the tube using acoustic spatial array signal processing techniques. The submersible meter enables real time measurement of the bubble size, the bubble surface area flux and flotation rate constant, which enables real time monitoring of the efficiency and recovery rate of flotation machines. A control system is also provided using the submersible meter improve the efficiency of mineral processing by controlling the process parameters in response to the measured parameter of the fluid within a flotation machine.

47 Claims, 13 Drawing Sheets

U.S. PATENT DOCUMENTS

| | | | |
|---|---|---|---|
| 3,952,578 A | 4/1976 | Jacobs | 73/64.1 |
| 4,004,461 A | 1/1977 | Lynworth | |
| 4,048,853 A | 9/1977 | Smith et al. | 73/861.25 |
| 4,080,837 A | 3/1978 | Alexander et al. | 73/61.45 |
| 4,195,517 A | 4/1980 | Kalinoski et al. | |
| 4,248,085 A | 2/1981 | Coulthard | 73/861.06 |
| 4,433,573 A | 2/1984 | Hulin | |
| 4,445,389 A | 5/1984 | Potzick et al. | 73/861.27 |
| 4,520,320 A | 5/1985 | Potzick et al. | |
| 4,561,310 A | 12/1985 | Barnard et al. | 73/861.02 |
| 4,677,305 A | 6/1987 | Ellinger | 73/290 V |
| 4,896,540 A | 1/1990 | Shakkottai et al. | 73/861.02 |
| 4,932,262 A | 6/1990 | Wlodarczyk | 250/227.3 |
| 5,040,415 A | 8/1991 | Barkhoudarian | 73/861.03 |
| 5,083,452 A | 1/1992 | Hope | 73/61 R |
| 5,146,414 A | 9/1992 | McKown et al. | |
| 5,218,197 A | 6/1993 | Carroll | 250/227.19 |
| 5,285,675 A | 2/1994 | Colgate et al. | 73/23.2 |
| 5,289,726 A | 3/1994 | Miau et al. | 73/861.22 |
| 5,359,897 A | 11/1994 | Hamstead et al. | 73/597 |
| 5,363,342 A | 11/1994 | Layton et al. | 367/149 |
| 5,367,911 A | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,526,844 A | 6/1996 | Kamen et al. | 137/614.11 |
| 5,591,922 A | 1/1997 | Segeral et al. | 73/861.04 |
| 5,660,977 A * | 8/1997 | Flores-Cotera et al. | 435/3 |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,856,622 A | 1/1999 | Yamamoto et al. | |
| 5,948,959 A | 9/1999 | Peloquin | 73/1.83 |
| 6,016,702 A | 1/2000 | Maron | 73/705 |
| 6,081,065 A | 6/2000 | Nabity et al. | |
| 6,151,958 A | 11/2000 | Letton et al. | |
| 6,202,494 B1 | 3/2001 | Riebel et al. | 73/861.29 |
| 6,216,532 B1 * | 4/2001 | Stephenson et al. | 73/152.21 |
| 6,349,599 B1 | 2/2002 | Lynnworth et al. | 73/644 |
| 6,354,147 B1 | 3/2002 | Gysling et al. | 73/61.79 |
| 6,378,357 B1 | 4/2002 | Han et al. | 73/54.41 |
| 6,397,683 B1 | 6/2002 | Hagenmeyer et al. | |
| 6,412,353 B1 | 7/2002 | Kleven et al. | 73/861.22 |
| 6,435,030 B1 | 8/2002 | Gysling et al. | 73/587 |
| 6,442,996 B1 | 9/2002 | Thurston et al. | 73/24.01 |
| 6,443,226 B1 | 9/2002 | Diener et al. | 166/241.6 |
| 6,450,037 B1 | 9/2002 | McGuinn et al. | 73/705 |
| 6,463,813 B1 | 10/2002 | Gysling | 73/862.59 |
| 6,532,827 B1 | 3/2003 | Ohnishi | |
| 6,536,291 B1 | 3/2003 | Gysling et al. | 73/861.42 |
| 6,550,342 B2 | 4/2003 | Croteau et al. | |
| 6,550,345 B1 * | 4/2003 | Letton | 73/861.27 |
| 6,558,036 B2 | 5/2003 | Gysling et al. | 374/147 |
| 6,575,043 B1 * | 6/2003 | Huang et al. | 73/861.25 |
| 6,587,798 B2 | 7/2003 | Kersey et al. | 702/50 |
| 6,601,005 B1 | 7/2003 | Eryurek et al. | 702/104 |
| 6,601,458 B1 | 8/2003 | Gysling et al. | 73/861.04 |
| 6,609,069 B2 | 8/2003 | Gysling | 702/48 |
| 6,658,945 B1 | 12/2003 | Kleven | 73/861.22 |
| 6,672,163 B2 * | 1/2004 | Han et al. | 73/597 |
| 6,691,584 B2 | 2/2004 | Gysling et al. | 73/861.42 |
| 6,698,297 B2 | 3/2004 | Gysling | 73/861.63 |
| 6,732,575 B2 | 5/2004 | Gysling et al. | 73/61.79 |
| 6,782,150 B2 | 8/2004 | Davis et al. | 385/12 |
| 6,813,962 B2 | 11/2004 | Gysling et al. | 73/861.26 |
| 6,837,098 B2 | 1/2005 | Gysling et al. | 73/61.79 |
| 6,837,332 B1 | 1/2005 | Rodney | 181/105 |
| 6,862,920 B2 | 3/2005 | Gysling et al. | 73/61.79 |
| 6,868,737 B2 | 3/2005 | Croteau et al. | |
| 6,889,562 B2 | 5/2005 | Gysling et al. | 73/861.42 |
| 6,898,541 B2 | 5/2005 | Gysling et al. | 902/100 |
| 6,945,095 B2 | 9/2005 | Johansen | |
| 6,950,760 B2 | 9/2005 | Henry et al. | |
| 6,959,604 B2 | 11/2005 | Davis et al. | |
| 6,971,259 B2 | 12/2005 | Gysling | |
| 6,988,411 B2 | 1/2006 | Gysling et al. | |
| 7,010,962 B2 * | 3/2006 | Sinha | 73/54.15 |
| 7,062,976 B2 | 6/2006 | Gysling et al. | |
| 7,086,278 B2 | 8/2006 | Gysling et al. | |
| 7,146,814 B2 | 12/2006 | Gilton | |
| 7,171,315 B2 * | 1/2007 | Loose | 702/45 |
| 2002/0064331 A1 | 5/2002 | Davis et al. | |
| 2002/0123852 A1 | 9/2002 | Gysling et al. | |
| 2002/0129662 A1 | 9/2002 | Gysling et al. | |
| 2003/0038231 A1 | 2/2003 | Bryant et al. | |
| 2003/0089161 A1 | 5/2003 | Gysling | |
| 2003/0136186 A1 | 7/2003 | Gysling et al. | |
| 2003/0154036 A1 | 8/2003 | Gysling et al. | |
| 2003/0235263 A1 | 12/2003 | Rajendran et al. | |
| 2004/0016284 A1 | 1/2004 | Gysling et al. | |
| 2004/0069069 A1 | 4/2004 | Croteau et al. | |
| 2004/0074312 A1 | 4/2004 | Gysling | |
| 2004/0144182 A1 | 7/2004 | Gysling et al. | |
| 2004/0167735 A1 | 8/2004 | Gysling et al. | |
| 2004/0168522 A1 | 9/2004 | Bailey et al. | |
| 2004/0168523 A1 | 9/2004 | Bailey et al. | |
| 2004/0194539 A1 | 10/2004 | Gysling | |
| 2004/0199340 A1 | 10/2004 | Gysling et al. | |
| 2004/0199341 A1 | 10/2004 | Gysling et al. | |
| 2004/0210404 A1 | 10/2004 | Gysling et al. | |
| 2004/0226386 A1 | 11/2004 | Croteau et al. | |
| 2004/0231431 A1 | 11/2004 | Bailey et al. | |
| 2004/0255695 A1 | 12/2004 | Gysling et al. | |
| 2005/0005711 A1 | 1/2005 | Curry et al. | |
| 2005/0005912 A1 | 1/2005 | Gysling et al. | |
| 2005/0005913 A1 | 1/2005 | Curry et al. | |
| 2005/0011258 A1 | 1/2005 | Didden et al. | |
| 2005/0011283 A1 | 1/2005 | Gysling et al. | |
| 2005/0011284 A1 | 1/2005 | Davis et al. | |
| 2005/0012935 A1 | 1/2005 | Kersey | |
| 2005/0033545 A1 | 2/2005 | Gysling | |
| 2005/0039520 A1 | 2/2005 | Bailey et al. | |
| 2005/0044929 A1 | 3/2005 | Banach et al. | |
| 2005/0044966 A1 | 3/2005 | Croteau et al. | |
| 2005/0050956 A1 | 3/2005 | Croteau et al. | |
| 2005/0061060 A1 | 3/2005 | Banach et al. | |
| 2005/0072216 A1 | 4/2005 | Engel | |
| 2005/0120799 A1 | 6/2005 | Gysling et al. | |
| 2005/0125166 A1 | 6/2005 | Davis et al. | |
| 2005/0125169 A1 | 6/2005 | Loose | |
| 2005/0125170 A1 | 6/2005 | Gysling | |
| 2005/0159904 A1 | 7/2005 | Loose et al. | |
| 2005/0171710 A1 | 8/2005 | Gysling et al. | |
| 2005/0227538 A1 | 10/2005 | Engel | |
| 2005/0249111 A1 | 11/2005 | Gysling et al. | |
| 2006/0037385 A1 | 2/2006 | Gysling | |
| 2006/0048583 A1 | 3/2006 | Gysling | |
| 2006/0053809 A1 | 3/2006 | Gysling et al. | |

FOREIGN PATENT DOCUMENTS

| | | |
|---|---|---|
| GB | 1578660 A | 11/1980 |
| JP | 07229964 A * | 8/1995 |
| JP | 2003043017 A * | 2/2003 |
| WO | WO 93/14382 | 7/1993 |
| WO | WO 00/00793 | 1/2000 |
| WO | WO 00/60317 | 10/2000 |
| WO | WO 01/02810 | 1/2001 |

OTHER PUBLICATIONS

"Sonar-Based Volumetric Flow Meter for Pulp and Paper Applications" by: Daniel L. Gysling and Douglas H. Loose—Dec. 3, 2002.

Sonar-Based Volumetric Flow Meter for Chemical and Petrochemical Applications by: Daniel L. Gysling and Douglas H. Loose—Feb. 14, 2003.

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.

"Viscous Attentuation of Acoustic Waves in Suspensions" by R.L. Gibson, Jr. and M.N. Toksoz.

"Flow Velocity Measurement using Spatial Filter" By: Yoshio Kurita, Takaharu Matsumoto and Yukitake Shibata, Nov. 1979.

"Dynamic Modelling of Gas Hold-Up in Different Electrolyte Systems" By: H. Kellermann, K. Juttner, G. Kreysa—Journal of Applied Electrochemistry 18 (1998) pp. 311-319.

"Estimation of Bubble Diameter in Flotation Columns from Drift Flux Analysis" G.S. Dobby, J.B. Yianatos and J.A. Finch, Canadian Metallurgical Quarterly, vol. 27, No. 2, pp. 895-90.

"Studies on Impeller Type, Impeller Speed and Air Flor Rate in an Industrial Scale Flotation Cell. Part 4: Effect of Bubble Surface Area Flux on Flotation Performance" B.K. Gorain, J.P. Franzidis, and E.V. Manlapig, Minerals Engineering vol. 10. No. 4 pp. 367-379.

"Gas Dispersion Measurements In Flotation Machines", C.O. Gomez and J.A. Finch, McGill University, Montreal Quebec, pp. 73-78.

Technical Note Reconciliation of Bubble Size Estimation Methods Using Drift Flux Analysis, S. Banisi and J.A. Finch, Minerals Engineering vol. 7 No. 12 pp. 1555-1559.

"New Flowmeter Principle"—By: Walt Boyes—Published in Flow Control Magazine—Oct. 2003 Issue.

"Piezoelectric Polymers"—By: J.S. Harrison and Z. Ounaies—ICASE Report.

* cited by examiner

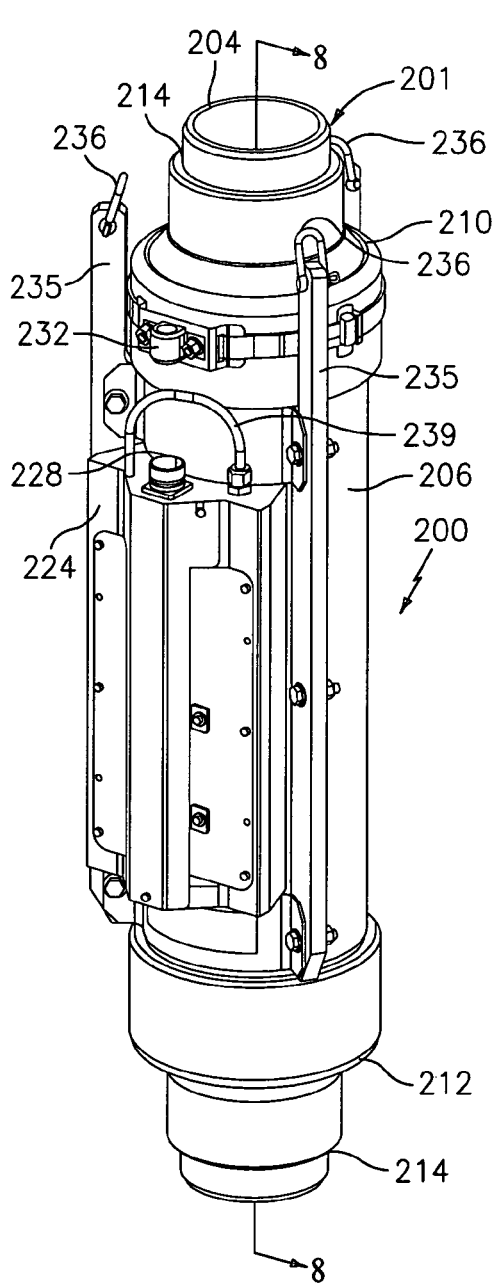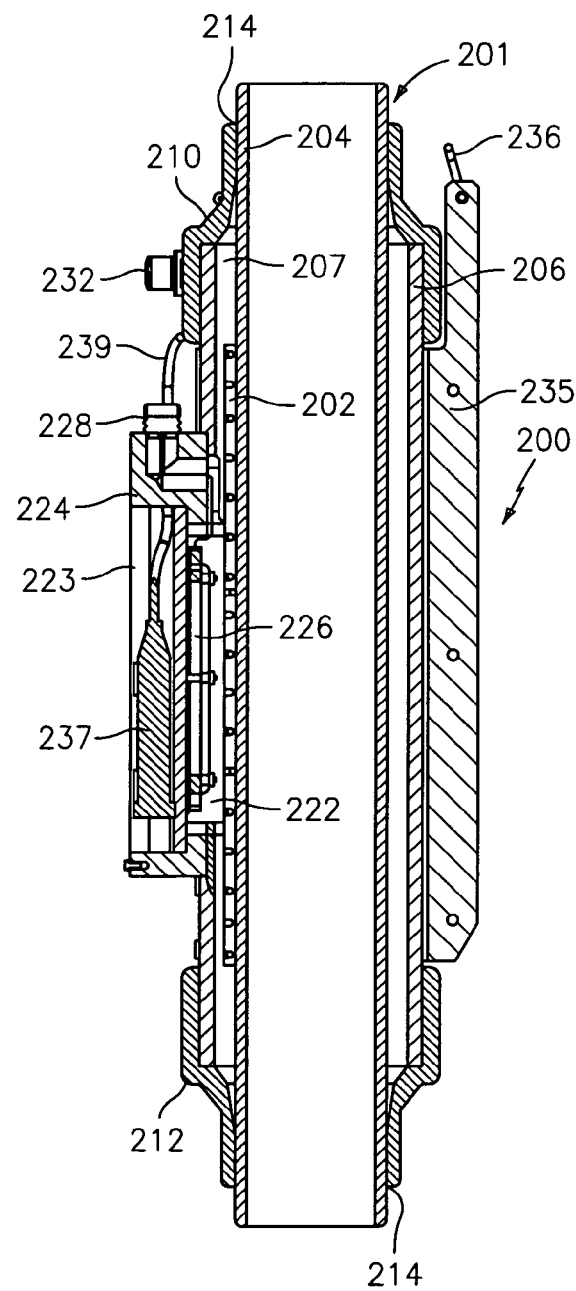
FIG. 7
FIG. 8

SUBMERSIBLE METER FOR MEASURING A PARAMETER OF GAS HOLD-UP OF A FLUID

CROSS-REFERENCE TO RELATED APPLICATIONS

The present invention claims the benefit of U.S. Provisional Patent Application Ser. No. 60/565,357 filed Apr. 26, 2004; U.S. Provisional Patent Application Ser. No. 60/587,610 filed Jul. 12, 2004; and U.S. Provisional Patent Application Ser. No. 60/634,326 filed Dec. 7, 2004, which are all incorporated herein by reference.

TECHNICAL FIELD

The present invention generally relates to a submersible meter for measuring a parameter of a flowing or static single and/or multi-phase fluid, such as the gas volume fraction, velocity, and volumetric flow of the liquid. The present invention is particularly useful in measuring the gas holdup and/or bubble surface area flux $S_b$ of an aerated multi-phase mixture or slurry within a mechanical tank or column cell used for minerals separation via flotation techniques.

BACKGROUND ART

The mineral processing industry uses a number of different methods to separate the desired minerals from other minerals and rocks. One such mineral processing system similar to that shown in FIG. 1 includes a mineral crusher, which crushes rocks and minerals to a size that is appropriate for the type of mineral being processed (approximately 250 µm for sulfide copper). The crushed rock and mineral is combined with water, a reagent, a frother, and a PH control to make a two-phase slurry (liquid and solids). This slurry is pumped into a mechanical flotation tank 1 for separation of the desired mineral (e.g., copper) from the other minerals and rocks. Gas is introduced at the bottom of the tank that is then chopped and mixed with the slurry by an impeller or mixer 2. This produces a means of floating minerals to the surface for extraction while sending other minerals to the bottom of the tank to exit through the tailings line 3. In some cases the desired mineral is floated to the surface, and in other cases it is recovered in the tailings. In the case where the desired mineral is floated, the proper reagent is selected to enable the mineral to attach to the rising bubbles 4. The bubbles then carry the mineral to the top of the flotation tank to thereby create a froth layer 5 with the desired mineral, which then is piped away or allowed to overflow into another receptacle.

Another method of separating the desired mineral from other minerals and rocks includes a column cell 6 similar to that shown in FIG. 2, which is another type of flotation machine that is sometimes used in combination with the mechanical flotation tank. In the column cell 6, the slurry is introduced at the top of the collection zone and flows down the column towards the bottom. Gas bubbles 4 are introduced at the bottom of the collection zone and slowly rise to the froth layer at the surface. The bubbles are generated using a sparging process. There is no mechanical agitation. The gas is typically expanded through a set of nozzles 7 to create bubbles, which can be accomplished either internal or external to the column. At the surface of the froth layer, wash water is sprayed down on the surface of the froth to control the bias in the column. As in the mechanical tank 1, the minerals in the froth layer 5 are collected in an overflow channel for further processing.

The amount and size of the bubbles 4 as well as the flow rate of the bubbles to the surface of the flotation tank/column cell are important parameters to know and control to provide the most efficient separation process of the ore. It would be advantageous to provide a submersible meter that can measure the gas holdup (i.e., gas volume fraction) of the fluid flowing from the bottom to the top of the tank, as well as the flow rate of the aerated fluid.

SUMMARY OF THE INVENTION

Objects of the present invention include providing a meter for measuring the speed of sound propagating through an aerated fluid or mixture to determine parameters of the fluid, such as the gas holdup ($\epsilon_g$) of the fluid, the bubble size ($d_b$), the bubble surface area flux ($S_b$), and the flotation rate constant (k).

According to the present invention, a submersible meter adapted to be disposed in an aerated fluid for measuring at least one parameter of the fluid is provided. The meter includes a tube having an open input end and an open output end for receiving a portion of the aerated fluid. A spatial array of at least two sensors, is disposed at different axial locations along the tube. Each sensor measures an acoustic pressure at a corresponding axial location and provides a measured signal indicative of the unsteady pressure at said axial location of a corresponding one of said sensors. A signal processor, responsive to said measured signals, provides a signal indicative of at least the gas holdup of the aerated fluid.

According to the present invention, a system for controlling the process of mineral processing is provided. The control system includes a submersible meter having a tube with an open input end and an open output end for receiving a portion of the aerated fluid. A spatial array of at least two sensors is disposed at different axial locations along the tube. Each of the sensors measure an acoustic pressure at a corresponding axial location and provides a measured signal indicative of the unsteady pressure at said axial location of a corresponding one of said sensors. A signal processor, responsive to said measured signals, provides an output signal indicative of at least the gas holdup of the aerated fluid. A control device receives the output signal and controls at least one process parameter to a desired level.

The foregoing and other objects, features and advantages of the present invention will become more apparent in light of the following detailed description of exemplary embodiments thereof.

BRIEF DESCRIPTION OF THE DRAWINGS

FIG. 7 is a perspective view of a submersible meter in accordance with the present invention.

FIG. 8 is a cross-sectional view of the submersible meter of FIG. 7 along line 8-8.

BEST MODE FOR CARRYING OUT THE INVENTION

Figure 1:
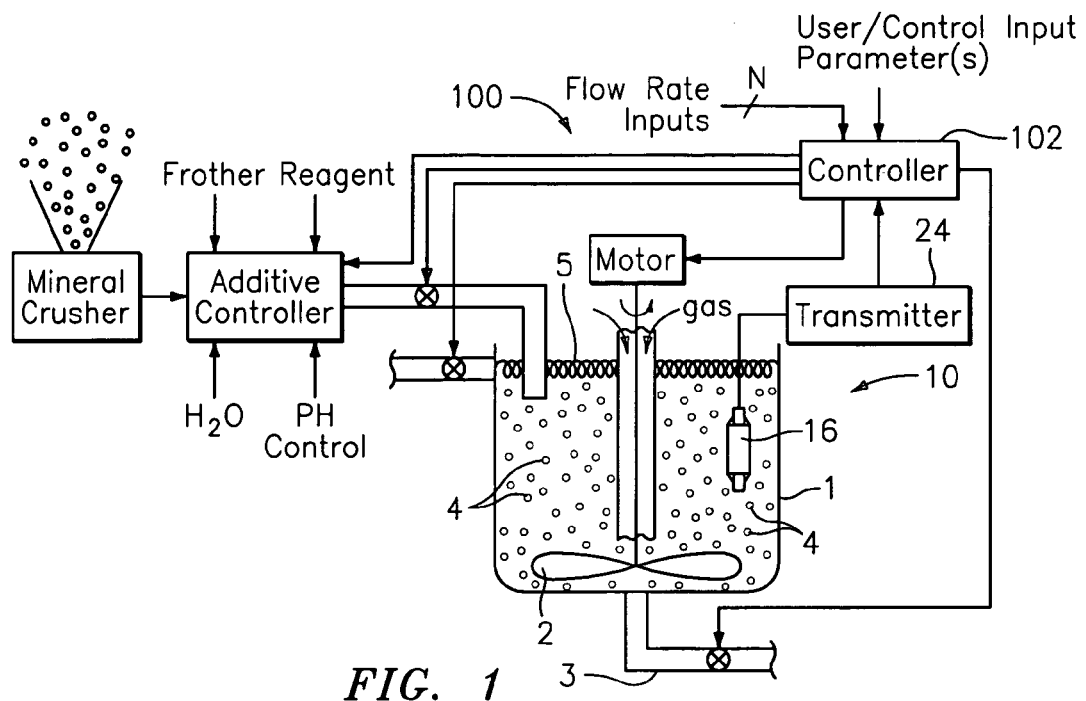
FIG. 1 is a schematic diagram of a closed loop control system for mineral processing embodying the present invention.
Figure 2:
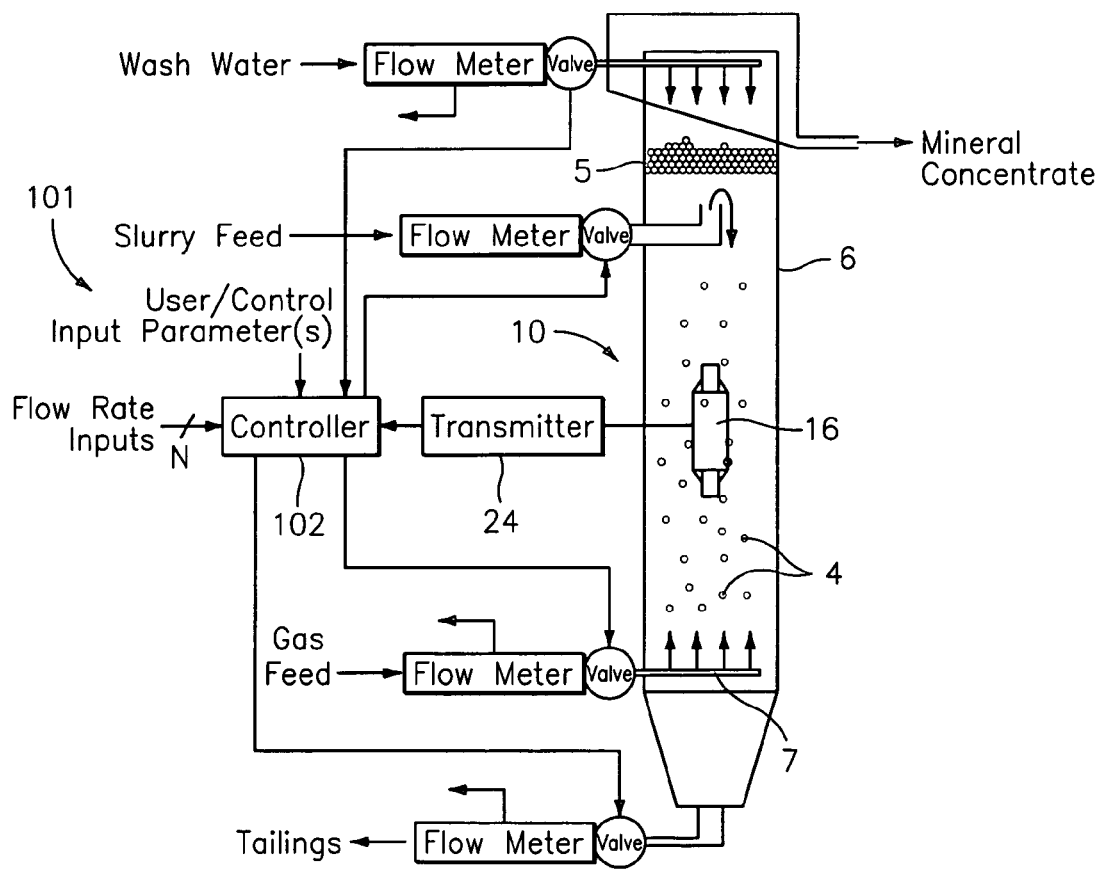
FIG. 2 is a schematic diagram of another closed loop control system for mineral processing embodying the present invention.
Figure 3:
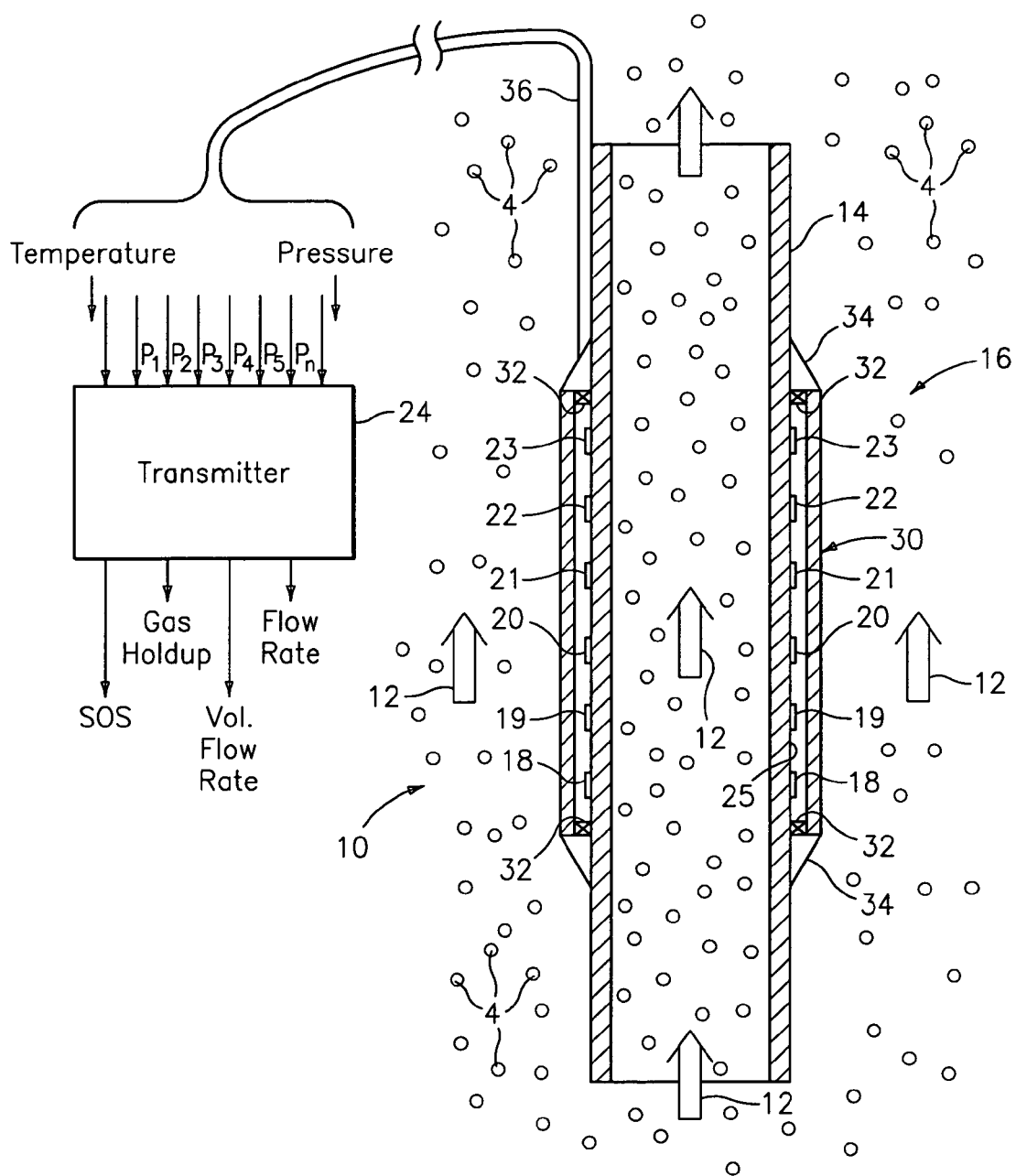
FIG. 3 is a schematic illustration of a submersible meter in accordance with the present invention.

Referring to FIGS. 1-3, a submersible meter, generally shown as 10, is provided to sense and determine specific characteristics or parameters of an aerated fluid 12 in a tank, a cell, a pipe or an unconfined space. The fluid 12 may be a single phase liquid, a mixture of multiple liquids, a mixture of solid(s)/liquid(s) or a combination thereof. One example of an aerated fluid that can be measured is a multiphase mixture having gas, liquid, minerals and rocks, such as that found in a minerals processing flotation machine. To simplify the description of the present invention, the submersible meter 10 will be described as a meter for measuring the parameter(s) of an aerated fluid comprising a mixture of liquids and solids. One will appreciate, however, that the meter may be used to measure specific characteristics of any aerated fluid and mixture. As will be described in greater detail, the meter measures the speed of sound propagating through the fluid to determine any one of a plurality of parameters of the fluid, such as the gas holdup of the fluid, bubble size, bubble surface area flux ($S_b$), the flotation rate constant (k), and speed of sound propagating through the fluid. Additionally, the meter 10 is capable of measuring the unsteady pressure disturbances (e.g., vortical effects, density changes) of the flow passing through the meter 10 to determine the rate and volumetric flow rate of the fluid.

FIG. 3 illustrates a schematic drawing of the meter 10 that includes a sensing device 16 comprising an inner tube 14 and an array of pressure sensors (or transducers) 18-23 spaced axially along the outer surface 25 of the inner tube 14. The pressure sensors measure the unsteady pressures produced by acoustical and/or vortical disturbances within the inner tube, which are indicative of a parameter of the fluid 12. The output signals ($P_1$-$P_6$) of the pressure sensors 18-23 are provided to a transmitter or processing unit 24, which processes the pressure measurement data and determines at least one parameter of the mixture. Specifically, the characteristics and parameters determined may include the gas holdup ($\epsilon_g$) of the fluid, bubble size ($d_b$), bubble surface area flux ($S_b$), the flotation rate constant (k), the speed of sound propagating through the fluid, the flow rate, and the volumetric flow rate.

In an embodiment of the present invention shown in FIG. 3, the meter 10 has six pressure sensors 18-23 disposed axially along the tube 14 for measuring the unsteady pressure $P_1$-$P_6$ of the fluid or mixture 12 flowing therethrough. The meter 10 has the ability to measure a parameter of the fluid using one or both of the following techniques described herein below:

1) Determining the speed of sound of acoustical disturbances or sound waves propagating through the flow 12 using the array of pressure sensors 18-23, and/or
2) Determining the velocity of vortical disturbances or "eddies" propagating through the flow 12 using the array of pressure sensors 18-23.

Generally, the first technique measures unsteady pressures created by acoustical disturbances propagating through the flow 12 to determine the speed of sound (SOS) propagating through the flow. Knowing the pressure and/or temperature of the flow (or estimating values for pressure and temperature) and the speed of sound of the acoustical disturbances, the processing unit 24 can determine the gas holdup of the aerated fluid 12, and other parameters, which will be described in greater detail hereinafter. The sensors and processing described herein is similar to that described in U.S. Pat. No. 6,354,147, U.S. Pat. No. 6,587,798, U.S. patent application Ser. No. 10/762,410, U.S. Pat. No. 7,062,976, and U.S. patent application Ser. No. 10/712,833, now abandoned, which are all incorporated herein by reference.

Figure 12:
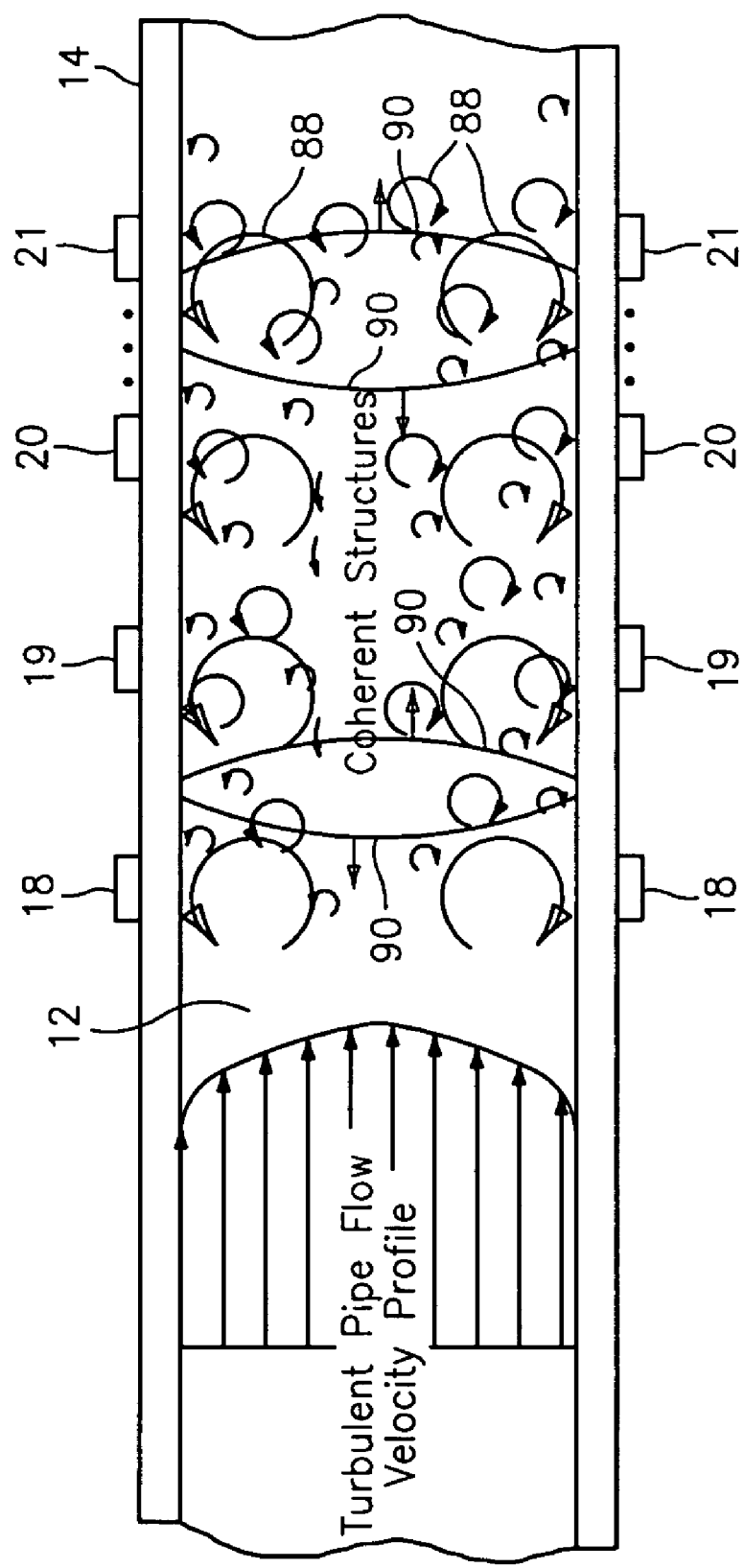
FIG. 12 is a cross-sectional view of a pipe showing a turbulent pipe flow velocity profile and acoustic wave propagating through a fluid.

The second technique measures the velocities associated with unsteady flow fields and/or pressure disturbances created by vortical disturbances or "eddies" to determine the velocity of the fluid 12. The pressure sensors 18-23 measure the unsteady pressures $P_1$-$P_6$ created by the vortical disturbances as these disturbances convect within the aerated fluid 12 through the meter 10 in a known manner, as shown in FIG. 12. Therefore, the velocity of these vortical disturbances is related to the velocity of the fluid 12 and hence the volumetric flow rate may be determined, as will be described in greater detail hereinafter.

The pressure sensors 18-23 may be disposed, directly attached or clamped onto the outer surface of the pipe, or may be ported through the walls of the pipe 14. The pressure sensors may be any one of the pressure sensors described in the aforementioned patents and patent applications. The pressure sensors are environmentally protected and acoustically protected by an outer pipe or housing 30 disposed coaxially with the inner pipe, similar to that described in U.S. Pat. No. 6,435,030 and U.S. patent application Ser. No. 10/412,839, which are incorporated herein by reference.

A pair of seals 32 are provided at the ends of the outer pipe 30 to seal the outer pipe to the inner pipe 14 to provide the isolated cavity around the sensors 18-23. A pair of conical end pieces 34 are mounted to the ends of the outer pipe to reduce drag across the sensor portion of the meter. A conduit 36 is provided to house the conductive wires between the pressure sensors and the transmitter 24.

The length of the pipe 14 is sufficient to accommodate the aperture or length of the sensor array 18-23. The inner pipe 14 is longer than the aperture length to permit the acoustic wave to set up in the inner pipe before propagating across the sensor array. The inner diameter of the inner pipe is dependent on the size and concentration of the bubbles 4. The larger the size of the bubbles the larger the diameter of the pipe. The greater the concentration, a smaller diameter of the pipe 14 may be possible (depending on the size of the bubbles). While the ends of the inner pipe are shown to be straight, the invention contemplates the ends of the inner pipe to expand or flare outwardly.

In the minerals processing industry, knowing the gas holdup within a flotation machine (e.g., flotation tank, column cell) is important to control the process of extracting the desired mineral(s) from the mined ore. To date, the industry is in need of a device that can accurately measure the gas holdup in a flotation machine in real time, which the present invention provides. As shown in FIGS. 1 and 2, the sensing device 16 of the meter 10 is disposed within the flotation machine 1,6 at a desired location and depth to measure the gas holdup in the fluid.

The performance of a flotation machine 1,6 (e.g., flotation cell and column cell) is primarily evaluated based on the grade and amount of the material produced. This is known as the grade/recovery relationship. The machine is also evaluated on its throughput capability as well as the resources required to achieve that level of performance. For example, these resources may include at least electrical power consumption and chemical usage.

It is understood that grade and recovery are dependent on the flotation rate constant (k), which is dependent on bubble surface area flux ($S_b$), as described in the article entitled "Studies on Impeller Type, Impeller Speed and Air Flow Rate in an Industrial Scale Flotation Cell. Part 4: Effect of Bubble Surface Area Flux on Flotation Performance" (1996) by Gorin, Franzidis, and Manlapig, which is incorporated herein by reference. The flotation rate constant is related to the recovery of the desired mineral by the following relationship:

$$k = R/[\tau - (1-R)] \quad \text{Eq. 1}$$

where

R=recovery of mineral

τ=mean residence time in cell k=flotation rate constant

The mean residence time is calculated as the ratio of the effective cell or tank volume (volume of air and impellor/stator mechanism minus the nominal cell/tank volume) and the feed flow rate.

The bubble surface area flux ($S_b$) is determined from gas holdup ($\epsilon_g$), superficial gas velocity ($J_g$), and bubble diameter ($d_b$), as described in the article entitled "Gas Dispersion Measurements in Flotation Machines", (2002) by Gomez and Finch; and the article entitled "Bubble Surface Area Flux: A Parameter to Characterize Flotation Cells" (1999) by Jum Finch, Cesar Gomez, Colin Harde, G. Leichtle, R. Filippone, and Donal Leroux, which are incorporated herein by reference. Bubble surface area flux is the surface area of bubbles per unit times per unit cross-sectional area of flotation machine. Specifically, bubble surface area flux is defined by:

$$S_b = 6(J_g)/d_b \quad \text{Eq. 2}$$

where $J_g = Q_g(A) Q_g$=gas rate; $A$=cell/tank cross-section $$\quad \text{Eq. 3}$$

To date, bubble size ($d_b$) and gas holdup ($\epsilon_g$) have been difficult to measure in real time in an industrial environment with non-transparent slurries. The present invention provides a robust real time measurement of the $\epsilon_g$ which enables a real time estimation of $d_b$ by using drift flux analysis, as described in the article entitled "Technical Note Reconciliation of Bubble Size Estimation Methods Using Drift Flux Analysis" (1987) by Banisi and Finch, and described in the article entitled "Estimation of Bubble Diameter in Flotation Columns from Drift Flux Analysis" (1987) by Dobby and Yianotos and Finch, which are incorporated herein by reference. Specifically, the bubble size is defined by the following:

$$d_b^2 = 18 \mu_f U_t (1 + 0.15 Re_s^{0.687})/[g \Delta \rho_f] \quad \text{Eq. 4}$$

where $$U_{sb} = (J_g/\epsilon_g) + (J_l/(1-\epsilon_g)) \quad \text{Eq. 5}$$

$$U_t = U_{sb}/(1-\epsilon_g)^{m-1} \quad \text{Eq. 6}$$

$$Re_s = [d_b U_{sb} \rho_f (1-\epsilon_g)]/\mu_f \quad \text{Eq. 7}$$

whereas $d_b$=bubble diameter, g=acceleration due to gravity, $J_g$=superficial gas velocity, $J_l$=superficial liquid velocity, $Re_s$=Reynolds number in a bubble swarm, $U_{sb}$=slip velocity between bubbles and liquid, $U_t$=bubble terminal velocity, $\epsilon_g$=fractional gas holdup, $\rho_f$=liquid density, $\mu_f$=liquid viscosity One method of bubble size estimation using drift flux analysis is to iteratively determine the bubble size ($d_b$) by first estimating the bubble size and determining the slip velocity ($U_{sb}$) using Eq. 5. Assuming m=3, the next step is to determine the Reynolds number in a swarm ($Re_s$) using Eq. 7. The bubble terminal velocity ($U_t$) is determined using Eq. 6 and Eq. 4. The bubble size ($d_b$) is iterated on using this method to determine the bubble size. While this is one method of using drift flux analysis to determine the bubble size, the present invention contemplates other method of using drift flux analysis as described in a previously cited reference.

By making a real time measurement of gas holdup ($\epsilon_g$), and using this to derive the bubble surface area flux ($S_b$), control optimization schemes may be used to yield improvements in flotation performance. Using this gas dispersion parameter, along with other easily attained gas, slurry, and wash water flow rates, closed loop control strategies may be employed to optimize the flotation process, as shown in FIGS. 1 and 2. In response to the signals from the submersible meter 10, flow measurements from flow meters disposed throughout the process, and a user/control input, a controller 100 may control motors, pumps and valves to control the speed of the mixer 2 in a mechanical tank 1, the gas flow rate, slurry flow rate, overflow rate, tailings flow rate, wash water, and chemical addition (e.g., frother, reagent PH control, and water). This will enable overall optimization of the grade and recovery performance parameters of the flotation process as well as the resources required to run the process.

Figure 4:
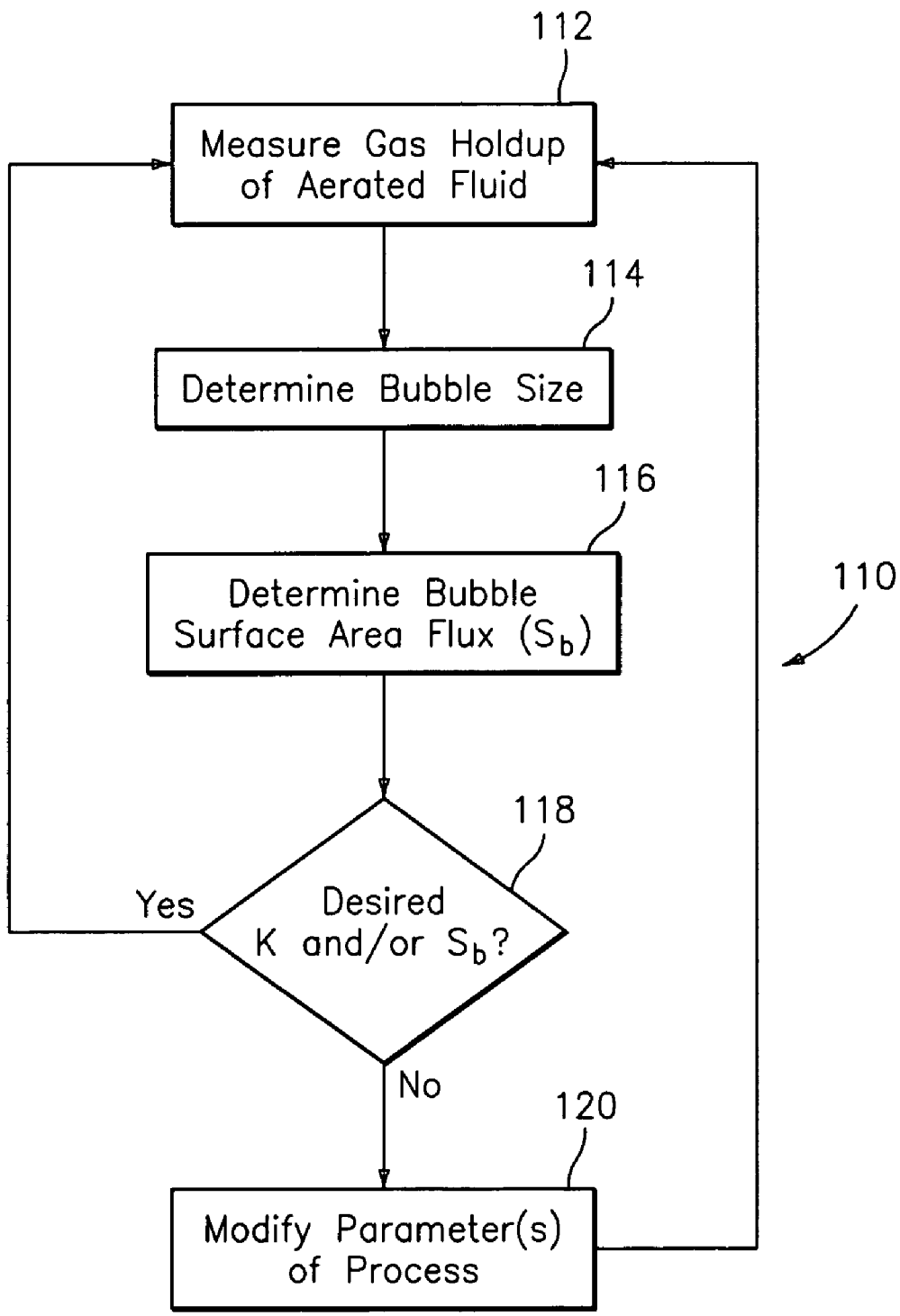
FIG. 4 is a flow diagram of the method determining a parameter of a fluid used in mineral processing and controlling the mineral processing in accordance with the present invention.

The controller 102 of the control systems 100,101 shown in FIGS. 1 and 2 optimizes the mineral processing system using the method 110 of FIG. 4. The controller 100, 101 in step 112 receives a signal from the submersible meter 10, which measures the gas holdup of the fluid 12 within the tank/column cell 1,6. The size of the bubbles ($d_b$) in step 114 is then determined using drift flux analysis as described hereinbefore. The controller in step 116, knowing the bubble size ($d_b$) and the gas holdup ($\epsilon_g$), determines the bubble surface area flux ($S_b$) that is indicative of the bubble dispersion and the flotation rate constant (k). The controller compares the bubble surface area flux and/or flotation rate constant to a desired parameter(s) in step 118. If the $S_b$ and/or k is within tolerance of a desired parameter, the controller does not change any parameters of the process and continues monitoring the bubble surface area flux and/or the flotation rate constant. If the bubble surface area flux and/or the flotation rate constant is not within the desired tolerance, the controller 102 in step 120 changes one or more parameters by changing flow rates of parameters described hereinbefore and/or changes the dosage of chemicals and additives to the process as described hereinbefore. The controller then continues to monitor the bubble surface area flux and/or the flotation rate constant. While the controller 102 has been described as determining parameters of the fluid, it is contemplated that the functions of the controller and the transmitter may be combined into a single processing/control device.

The mechanical flotation tank 1 may include a control valve and volumetric flow meter to control the gas inlet to the tank, a control valve and volumetric flow meter to control the slurry input to the tank, a control valve and volumetric flow meter to control the tailings output from the tank, and a motor driven mixer to chop and mix the gas bubbles with the slurry.

The column cell 6 may include a control valve and volumetric flow meter to control the gas inlet to the column, a control valve and volumetric flow meter to control the slurry input to the column, a control valve and volumetric flow meter to control the tailings output from the column, a control valve and volumetric flow meter to control the wash water, and a level indicator in the column.

Figure 5:
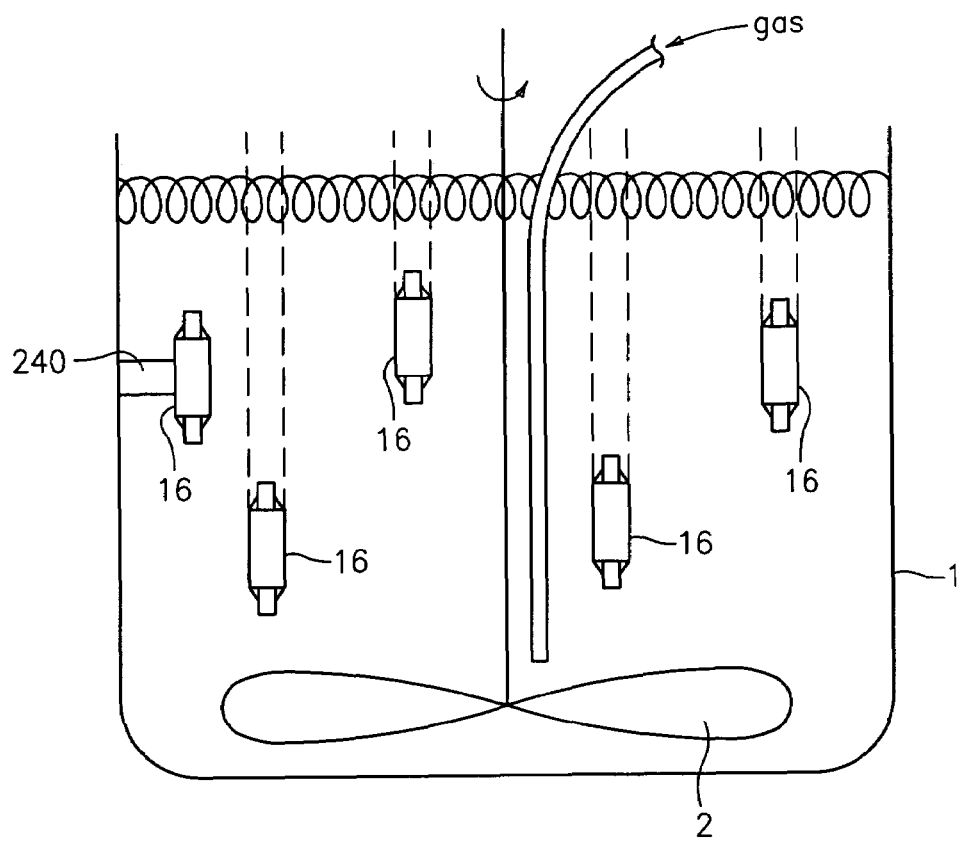
FIG. 5 is a side elevational view of a flotation tank having a plurality of submersible meters disposed at different locations and depths in the tank in accordance with the present invention.
Figure 6:
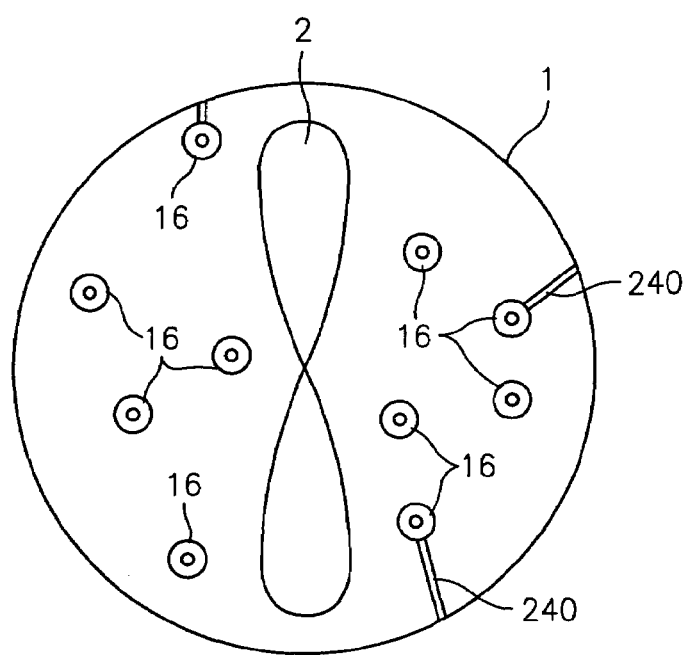
FIG. 6 is a top plan view of a flotation tank having a plurality of submersible meters disposed at different locations and depths in the tank in accordance with the present invention.

In addition, the submersible meter 10 may be used to map out the gas holdup ($\epsilon_g$) within a mechanical tank 1 or a column cell 2 by moving the meter 10 around to different locations and depths. This mapping of the gas holdup will enable predicative maintenance of the bubble generation equipment as well as research on new bubble generation designs. Referring to FIGS. 5 and 6, it is also contemplated that multiple meters 10 may be disposed within the tank/column cell at many locations at varying depths within the cell or tank. The sensing portions 16 may be suspended within the cell or tank by an attachment or physically mounted to the wall of the tank/cell as shown.

FIG. 7 shows a perspective view of another embodiment of the sensing portion 201 of a submersible meter 200 embodying the present invention. As best shown in FIG. 8, the sensing portion 202 includes an array of sensors 202 clamped onto an inner pipe 204. The length of the pipe is approximately 35 inches long having an outer diameter of 4 inches. The pipe is formed of a plastic material (e.g., PVC, schedule 40). The outer housing 206 is approximately 25 inches long having an outer diameter of approximately 6.5 inches, and formed of PVC schedule 80. While the sensing portion is formed primarily of plastic (including a circuit board housing 224), it is contemplated that components of the sensing portion 202 may be formed of metal (e.g., stainless steel), plastic or compounded material. However, the reliability and lifespan of the sensing portion is increased when using plastic components when submersed in corrosive or harsh fluids. Each sensor comprises a strip of piezoelectric sheet material (e.g., PVDF), similar to that described in U.S. patent application Ser. No. 10/712,833, filed Nov. 12, 2003; now abandoned, and U.S. patent application Ser. No. 10/712,818, filed Nov. 12, 2003, which are incorporated herein by reference. While the piezoelectric film material is mounted to a strap for mounting to the pipe 204, the invention contemplates that the piezoelectric sheet material may be attached directly to the pipe or embedded therein.

As best shown in FIGS. 7 and 8, a housing 206 is mounted onto the pipe 204 to environmentally and acoustically insulate the sensors 202. The housing prevents fluid from entering the cavity 207 surrounding the sensors (see FIG. 8), which is formed by the housing. The housing includes a generally cylindrical tube having a pair of end caps 210,212. The end caps have a hole (214) disposed in the outer wall of the end cap for receiving the pipe 204. The end caps are installed on the pipe 204 and welded, epoxied, glued or otherwise adhered together to prevent the passage of fluid within the inner cavity.

One wall of the housing tube 206 includes an opening 222 to provide access of an electrical conduit or wires to the sensors 202. A circuit board housing 224 is provided that comprises a single bored out piece wherein a circuit board 226 (e.g., pre-amplifier board 39) is mounted thereto and a fluid proof connector 228 mounted to the circuit board housing. The circuit board housing and the housing tube are secured together by welding or an adhesive. A pressure sensor 237 is disposed in an outer cavity 223 of the circuit board housing 224. A cable 239 extends from the circuit board 226 to the pressure sensor 237.

A cable relief device or cable mount 232 is mounted to an end cap for securing the cable 234 therein. The sensing portion 201 also includes three bars 235 mounted longitudinally to the housing 206 being circumferentially spaced evenly. The bars 235 are formed of a metal or other heavy material to provide sufficient weight to prevent the sensing portion 201 from floating. A U-bolt 236 extends from the ends of each bar 235. The U-bolts provide a means to hang or support the meter within the fluid 12 being measured. Alternatively, as mentioned, the meter may have means 240 for rigidly mounting the meter to another structure, such as the wall of a tank 1 or column cell 6, as shown in phantom lines in FIGS. 5 and 6.

Figure 9:
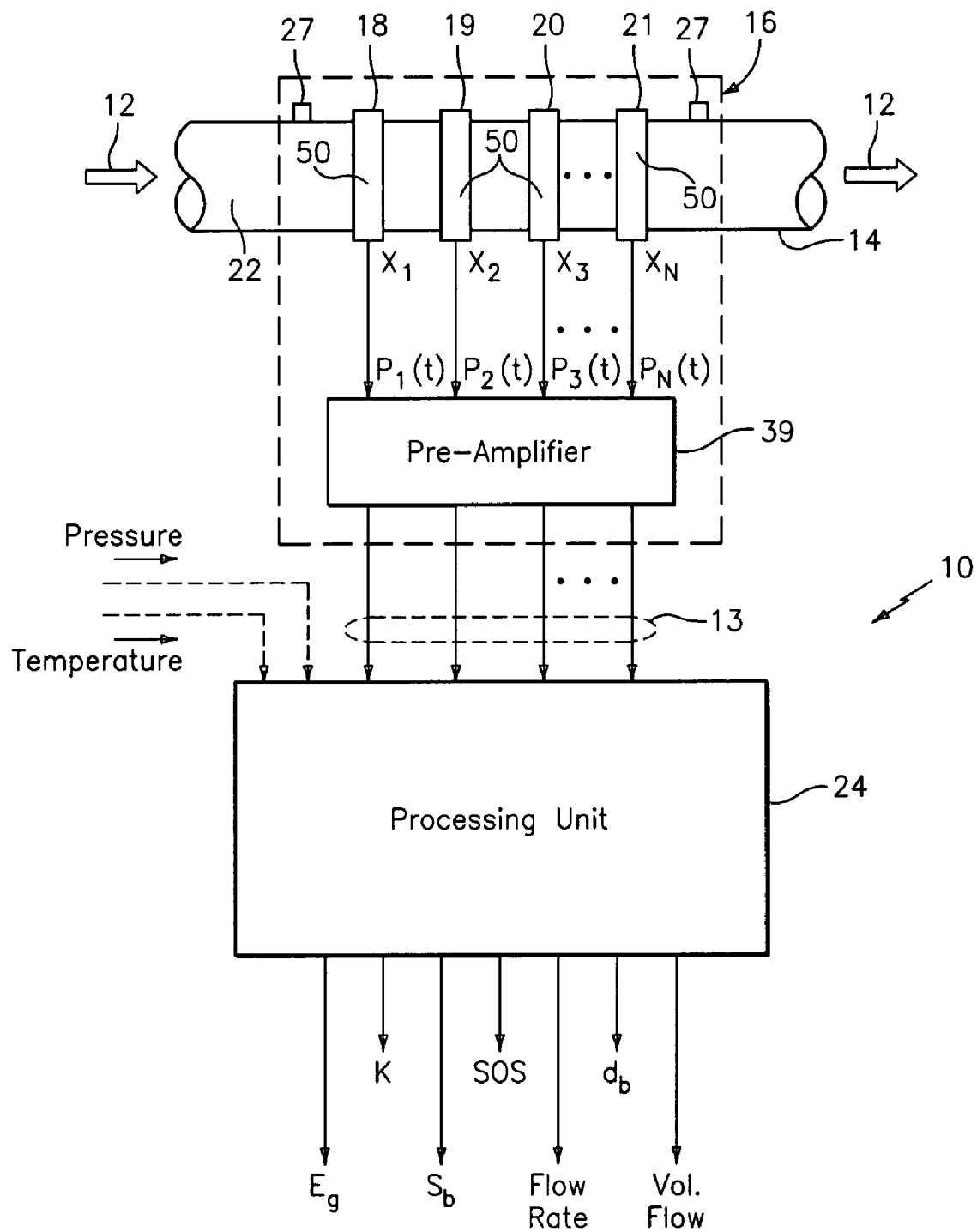
FIG. 9 is a schematic diagram of a submersible meter in accordance with the present invention.

FIG. 9 shows a block diagram of the submersible meter 10 described in the embodiments hereinbefore. The meter 10 includes a sensing device 16 and a processing unit 24 (or transmitter). The sensing device 16 comprises an array of strain-based sensors or pressure sensors 18-21 for measuring the unsteady pressures produced by acoustic waves propagating through the fluid and/or by vortical disturbances within the pipe, which are indicative of parameters and/or characteristics of the process flow 12. The output signals ($P_1(t)$-$P_N(t)$) of the pressure sensors 18-21 are provided to a pre-amplifier unit 39 that amplifies the signals generated by the pressure sensors 18-21. The processing unit 24 processes the pressure measurement data $P_1(t)$-$P_N(t)$ and determines the desired parameters and characteristics of the flow 12, as described hereinbefore. A cable 13 electronically connects the sensing device 16 to the processing unit 24. The analog pressure sensor signals $P_1(t)$-$P_N(t)$ are typically 4-20 mA current loop signals.

The array of pressure sensors 18-21 comprises at least two pressure sensors 18,19 spaced axially along the outer surface 22 of the pipe 14. The pressure sensors 18-21 may be clamped onto or generally removably mounted to the pipe by any releasable fastener, such as bolts, screws and clamps. Alternatively, the sensors may be permanently attached to or integral (e.g., embedded) with the pipe 14. The array of sensors of the sensing device 16 may include any number of pressure sensors 18-21 greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the flow. Therefore, the number of sensors used is dependent at least on the degree of accuracy desired and the desired update rate of the output parameter provided by the apparatus 10. The pressure sensors 18-19 measure the unsteady pressures produced by acoustic waves propagating through the flow, which are indicative of the SOS propagating through the fluid 12, and/or the pressure disturbances (e.g., vortical eddies) that convect with the fluid, which are indicative of the velocity of the disturbances propagating through the fluid 12, respectively.

The submersible meter 10 also contemplates providing one or more acoustic sources 27 to enable the measurement of the speed of sound propagating through the flow for instances of acoustically quiet flow. The acoustic source may be a device that taps or vibrates on the wall of the pipe, for example. The acoustic sources may be disposed at the input end of output end of the array of sensors 18-21, or at both ends as shown. One should appreciate that in most instances the acoustics sources are not necessary and the apparatus passively detects the acoustic ridge provided in the flow 12, as will be described in greater detail hereinafter. The passive noise includes noise generated by pumps, valves, motors, mixers, and the turbulent mixture itself.

As suggested and further described in greater detail hereinafter, the apparatus 10 has the ability to measure the speed of sound (SOS) and/or flow rate (or velocity) using one or both of the following techniques described herein below:

1) Determining the speed of sound of acoustical disturbances or sound waves propagating through the flow 12 using the array of pressure sensors 18-21, and/or
2) Determining the velocity of pressure disturbances (e.g., vortical eddies) propagating through the flow 12 using the array of pressure sensors 18-21.

Generally, the first technique measures unsteady pressures created by acoustical disturbances propagating through the flow 12 to determine the speed of sound (SOS) propagating through the flow. Estimating or measuring the pressure and/or temperature of the fluid and the speed of sound of the acoustic disturbances or waves, the processing unit 24 can determine the gas holdup ($\epsilon_g$) of the fluid, bubble size ($d_b$), bubble surface area flux ($S_b$), the flotation rate constant (k), the speed of sound propagating through the fluid, the flow rate, and the volumetric flow rate, such as that described in U.S. patent application Ser. No. 10/349,716, filed Jan. 23, 2003, U.S. Pat. No. 7,032,432 and, U.S. Pat. No. 7,062,976, which are all incorporated by reference.

The second technique measures the velocities associated with unsteady flow fields and/or pressure disturbances, such as that created by vortical disturbances or "eddies" 88 (see FIG. 12) that convect with the fluid 12 to determine the velocity of the fluid. The pressure sensors 18-21 measure the unsteady pressures $P_1$-$P_N$ created by the vortical disturbances 88, for example, as these disturbances convect with the fluid 12 through the pipe 14 in a known manner, as shown in FIG. 12. Therefore, the velocity of these vortical disturbances is related to the velocity of the flow 12 and hence the volumetric flow rate may be determined, as will be described in greater detail hereinafter.

Figure 10:
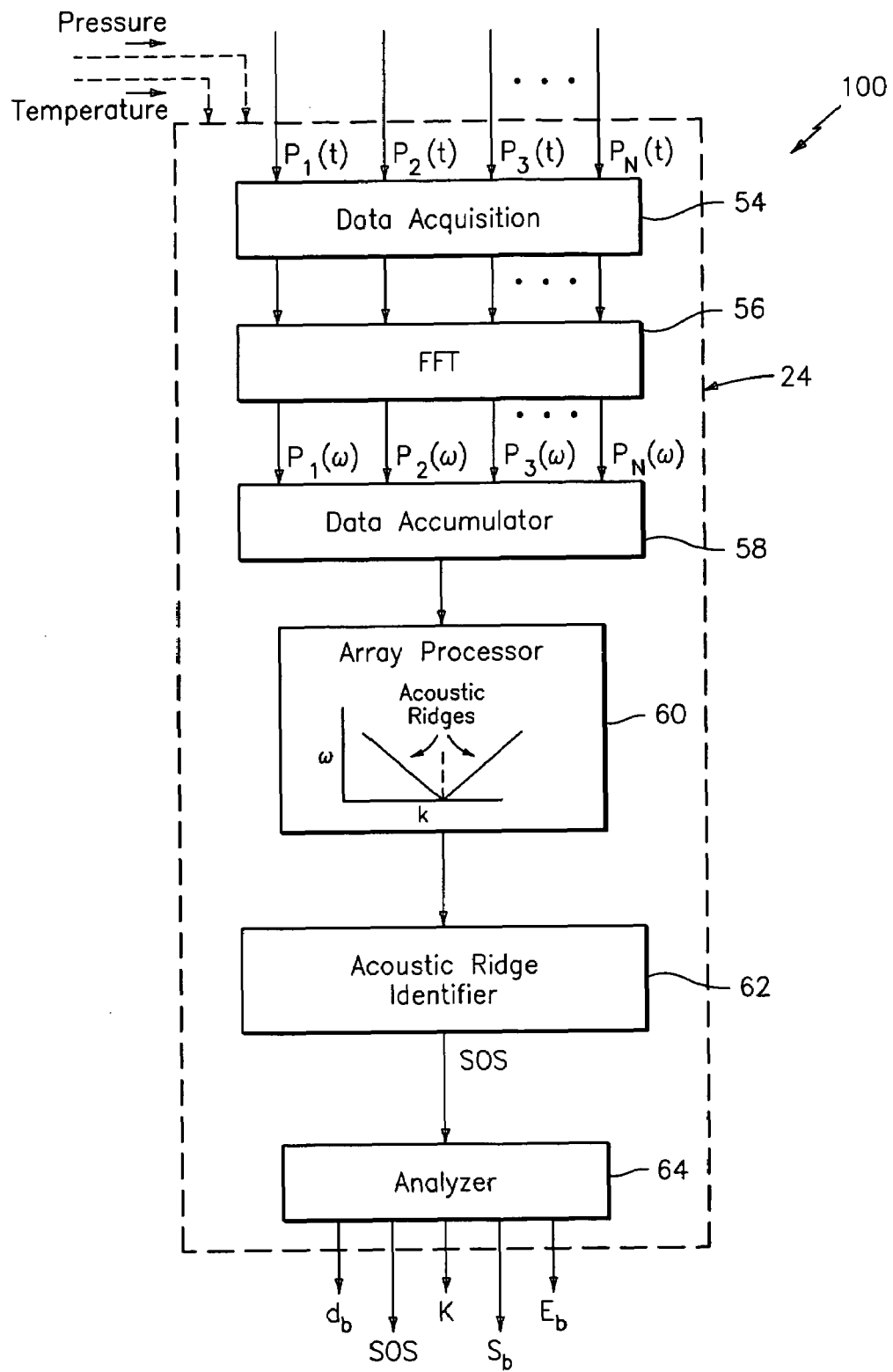
FIG. 10 is a block diagram of the processing unit of a submersible meter in accordance with the present invention.

Referring to FIG. 10, the processing unit 24 processes the pressure signals $P_1(t)$-$P_N(t)$ to first provide output signals indicative of the speed of sound propagating through the fluid 12, and subsequently, provide output signals in response to pressure disturbances generated by acoustic waves propagating through the flow 12, such as gas holdup ($\epsilon_b$), flotation rate constant (k), bubble surface area flux ($S_b$), and bubble size ($d_b$) of the aerated fluid 12.

The processing unit 24 receives the pressure signals from the array of sensors 18-21. A data acquisition unit 54 digitizes pressure signals $P_1(t)$-$P_N(t)$ associated with the acoustic waves 90 propagating through the pipe 14. An FFT logic 56 calculates the Fourier transform of the digitized time-based input signals $P_1(t)$-$P_N(t)$ and provides complex frequency domain (or frequency based) signals $P_1(\omega),P_2(\omega),P_3(\omega)),P_N(\omega)$ indicative of the frequency content of the input signals. A data accumulator 58 accumulates the additional signals $P_1(t)$-$P_N(t)$ from the sensors, and provides the data accumulated over a sampling interval to an array processor 60, which performs a spatial-temporal (two-dimensional) transform of the sensor data, from the xt domain to the k-ω domain, and then calculates the power in the k-ω plane, as represented by a k-ω plot, similar to that provided by the convective array processor 46 of FIG. 13.

To calculate the power in the k-ω plane, as represented by a k-ω plot (see FIG. 11) of either the signals or the differenced signals, the array processor 60 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensors 18-21.

Figure 11:
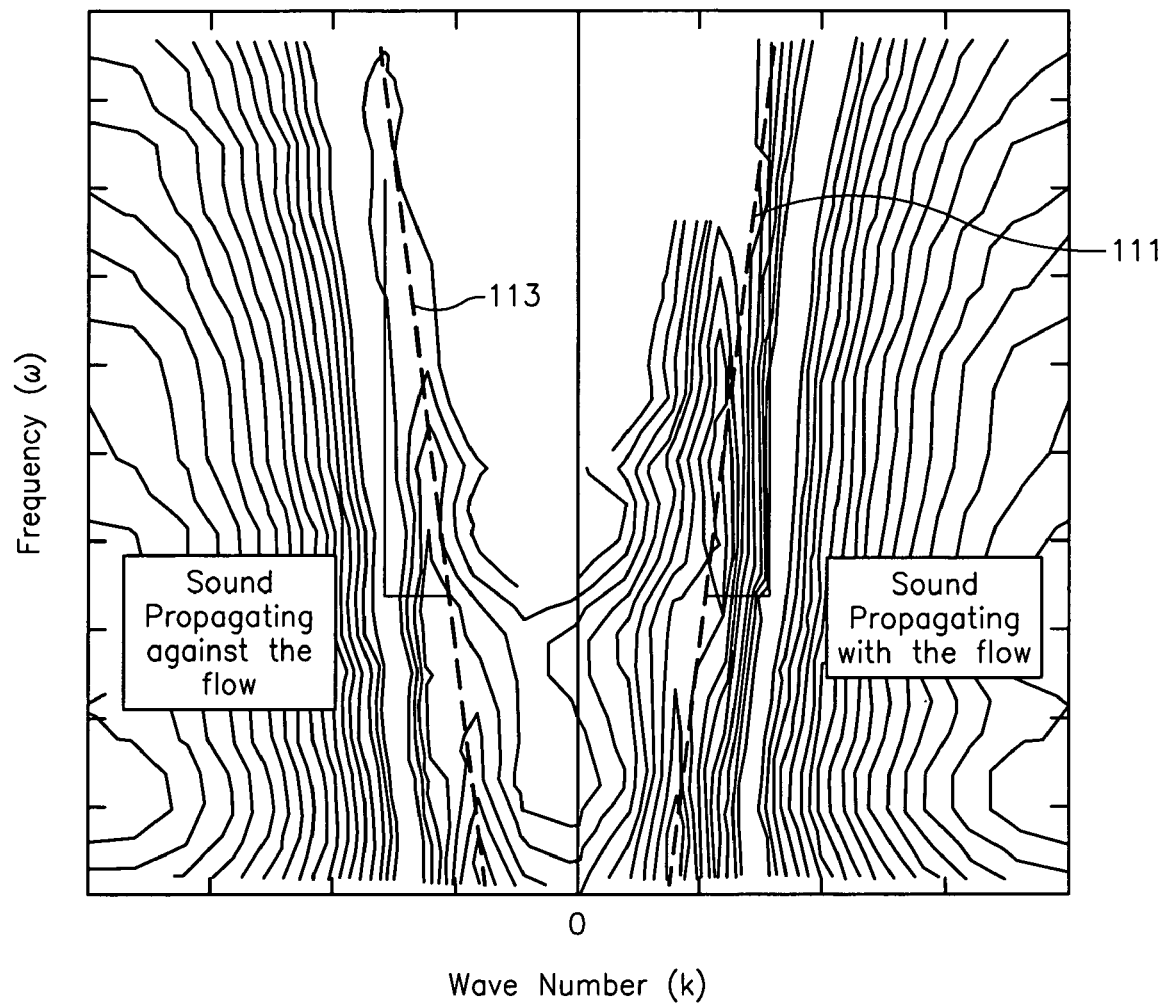
FIG. 11 is a kω plot of data processed from an array of pressure sensors used to measure the speed of sound propagating through a fluid within the submersible meter, in accordance with the present invention.

In the case of suitable acoustic waves 90 being present in both axial directions, the power in the k-ω plane shown in a k-ω plot of FIG. 11 so determined will exhibit a structure that is called an acoustic ridge 111,113 in both the left and right planes of the plot, wherein one of the acoustic ridges 111 is indicative of the speed of sound traveling in one axial direction and the other acoustic ridge 113 being indicative of the speed of sound traveling in the other axial direction. The acoustic ridges represent the concentration of a stochastic parameter that propagates through the fluid 12 and is a mathematical manifestation of the relationship between the spatial variations and temporal variations described above. Such a plot will indicate a tendency for k-ω pairs to appear more or less along a line 111,113 with some slope, the slope indicating the speed of sound.

The power in the k-ω plane so determined is then provided to an acoustic ridge identifier 62, which uses one or another feature extraction method to determine the location and orientation (slope) of any acoustic ridge present in the left and right k-ω plane. The velocity may be determined by using the slope of one of the two acoustic ridges 111,113 or averaging the slopes of the acoustic ridges 111,113.

Finally, information including the acoustic ridge orientation (slope) is used by an analyzer 64 to determine the flow parameters relating to measured speed of sound, such as gas holdup ($\epsilon_b$), flotation rate constant (k), bubble surface area flux ($S_b$), and bubble size ($d_b$) of the aerated fluid 12.

Figure 13:
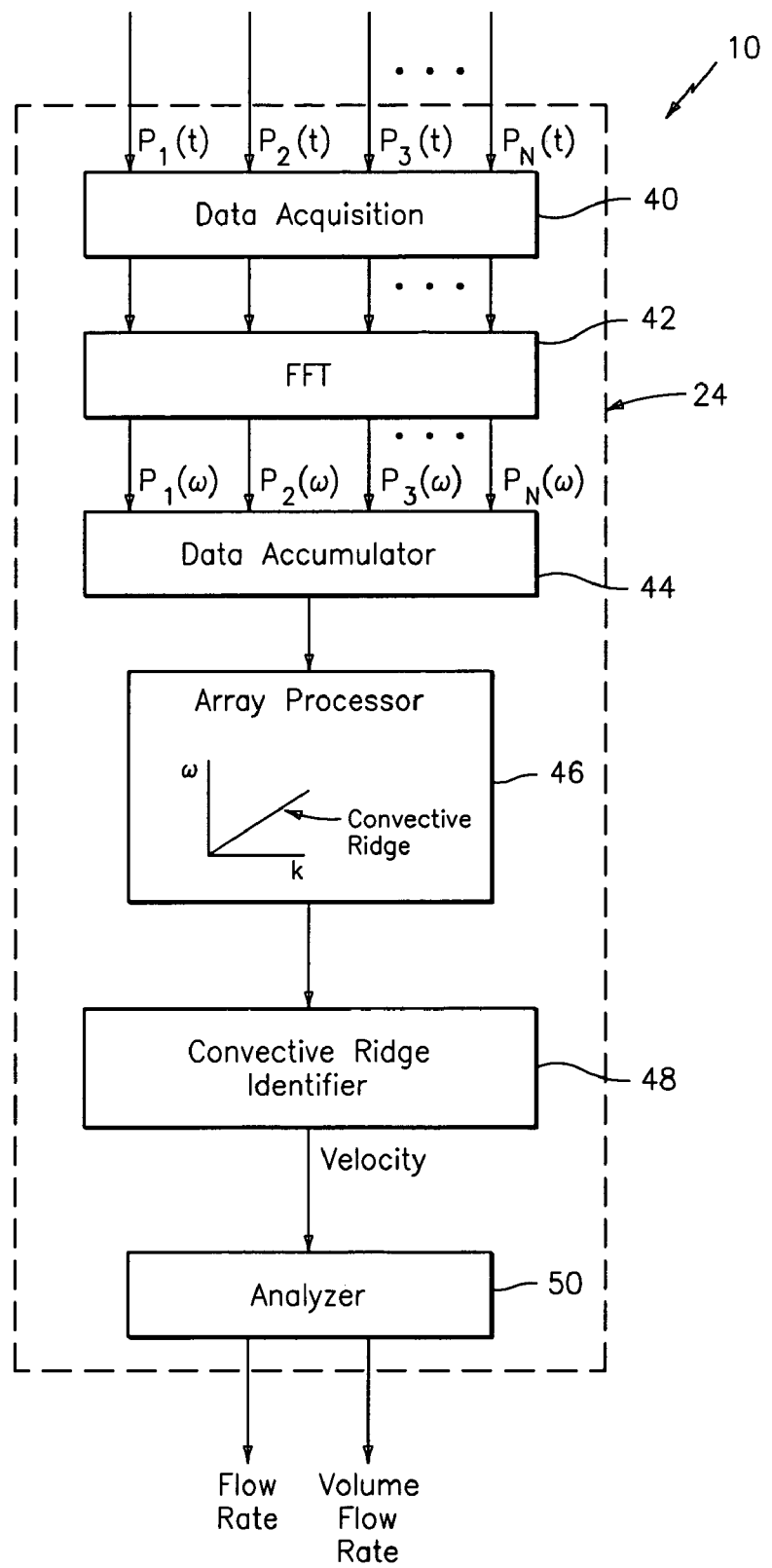
FIG. 13 is a block diagram of the processing unit of a submersible meter in accordance with the present invention.

Similar to the array processor 46 of FIG. 13, the array processor 60 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by k=2π/λ where λ is the wavelength of a spectral component, and corresponding angular frequencies given by ω=2πν.

One such technique of determining the speed of sound propagating through the flow 12 is using array processing techniques to define an acoustic ridge in the k-ω plane as shown in FIG. 11. The slope of the acoustic ridge is indicative of the speed of sound propagating through the fluid 12. The speed of sound (SOS) is determined by applying sonar array-ing processing techniques to determine the speed at which the one dimensional acoustic waves propagate past the axial array of unsteady pressure measurements distributed along the inner pipe 14.

The submersible meter 10 of the present invention measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and fluid 12 may be determined using a number of known techniques, such as those set forth in U.S. Pat. No. 6,354,147; U.S. Pat. No. 7,146,864; U.S. Pat. No. 6,587,798; U.S. Pat. No. 6,732,575, and U.S. Pat. No. 7,062,976, each of which are incorporated herein by reference.

While the sonar-based flow meter using an array of sensors 18-21 to measure the speed of sound of an acoustic wave propagating through the mixture is shown and described, one will appreciate that any means for measuring the speed of sound of the acoustic wave may be used to determine the gas holdup (or entrained gas volume fraction) of the fluid or other characteristics of the fluid described hereinbefore.

The analyzer 64 of the processing unit 24 provides output signals indicative of characteristics of the fluid 12 that are related to the measured speed of sound (SOS) propagating through the fluid. For example, to determine the gas holdup, the analyzer 64 assumes a nearly isothermal condition for the fluid 12. As such the gas holdup is related to the speed of sound by the following quadratic equation:

$$Ax^2+Bx+C=0$$

wherein x is the speed of sound, $A=1+rg/rl*(K_{eff}/P-1)-K_{eff}/P$, $B=K_{eff}/P-2+rg/rl$; $C=1-K_{eff}/rl*a_{meas}{}^2)$; Rg=gas density, rl=liquid density, $K_{eff}$=effective K (modulus of the liquid and pipewall), P=pressure, and $a_{meas}$=measured speed of sound.

Effectively, $$\text{Gas Holdup } (\epsilon_g)=(-B+\text{sqrt}(B^2-4*A*C))/(2*A)$$

Alternatively, the sound speed of a mixture can be related to volumetric phase fraction ($\phi_i$) of the components and the sound speed (a) and densities ($\rho$) of the component through the Wood equation.

$$\frac{1}{\rho_{mix}a_{mix\infty}^2} = \sum_{i=1}^{N} \frac{\phi_i}{\rho_i a_i^2} \text{ where } \rho_{mix} = \sum_{i=1}^{N} \rho_i \phi_i$$

One dimensional compression waves propagating within a mixture 12 contained within a pipe 14 exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{\frac{1}{a_{mix\infty}^2} + \rho_{mix}\frac{2R}{Et}}} \quad (\text{eq 1})$$

The mixing rule essentially states that the compressibility of a mixture ($1/(\rho a^2)$) is the volumetrically-weighted average of the compressibilities of the components. For gas/liquid mixtures 12 at pressure and temperatures typical of paper and pulp industry, the compressibility of the gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas.

Similar to the processing unit 24 of FIG. 10, the processing unit 24 of FIG. 13 receives the pressure signals from the array of sensors 18-21. A data acquisition unit 40 (e.g., A/D converter) converts the analog signals to respective digital signals. The FFT logic calculates the Fourier transform of the digitized time-based input signals $P_1(t)$–$P_N(t)$ and provides complex frequency domain (or frequency based) signals $P_1(\omega),P_2(\omega),P_3(\omega),P_N(\omega)$ indicative of the frequency content of the input signals. Instead of FFT's, any other technique for obtaining the frequency domain characteristics of the signals $P_1(t)$-$P_N(t)$, may be used. For example, the cross-spectral density and the power spectral density may be used to form frequency domain transfer functions (or frequency response or ratios) discussed hereinafter.

One technique of determining the convection velocity of the turbulent eddies 88 within the process flow 12 is by characterizing a convective ridge of the resulting unsteady pressures using an array of sensors or other beam forming techniques, similar to that described in U.S. Pat. No. 6,889,562 and U.S. Pat. No. 6,609,069, which are incorporated herein by reference.

A data accumulator 44 accumulates the frequency signals $P_1(\omega)$-$P_N(\omega)$ over a sampling interval, and provides the data to an array processor 46, which performs a spatial-temporal (two-dimensional) transform of the sensor data, from the xt domain to the k-$\omega$ domain, and then calculates the power in the k-$\omega$ plane, as represented by a k-$\omega$ plot.

The array processor 46 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length.

Convective characteristics or parameters have a dispersion relationship that can be approximated by the straight-line equation, $$k=\omega/u,$$

where u is the convection velocity (flow velocity). A plot of k-$\omega$ pairs is obtained from a spectral analysis of sensor samples associated with convective parameters. The pairings are portrayed so that the energy of the disturbance spectrally corresponding to the pairings can be described as a substantially straight ridge, a ridge that in turbulent boundary layer theory is called a convective ridge. What is being sensed are not discrete events of turbulent eddies, but rather a continuum of possibly overlapping events forming a temporally stationary, essentially white process over the frequency range of interest. In other words, the convective eddies 88 are distributed over a range of length scales and hence temporal frequencies.

To calculate the power in the k-ω plane, as represented by a k-ω plot (see FIG. 14) of either the signals, the array processor 46 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 18-21.

The present invention may use temporal and spatial filtering to precondition the signals to effectively filter out the common mode characteristics $P_{common\ mode}$ and other long wavelength (compared to the sensor spacing) characteristics in the pipe 14 by differencing adjacent sensors and retaining a substantial portion of the stochastic parameter associated with the flow field and any other short wavelength (compared to the sensor spacing) low frequency stochastic parameters.

Figure 14:
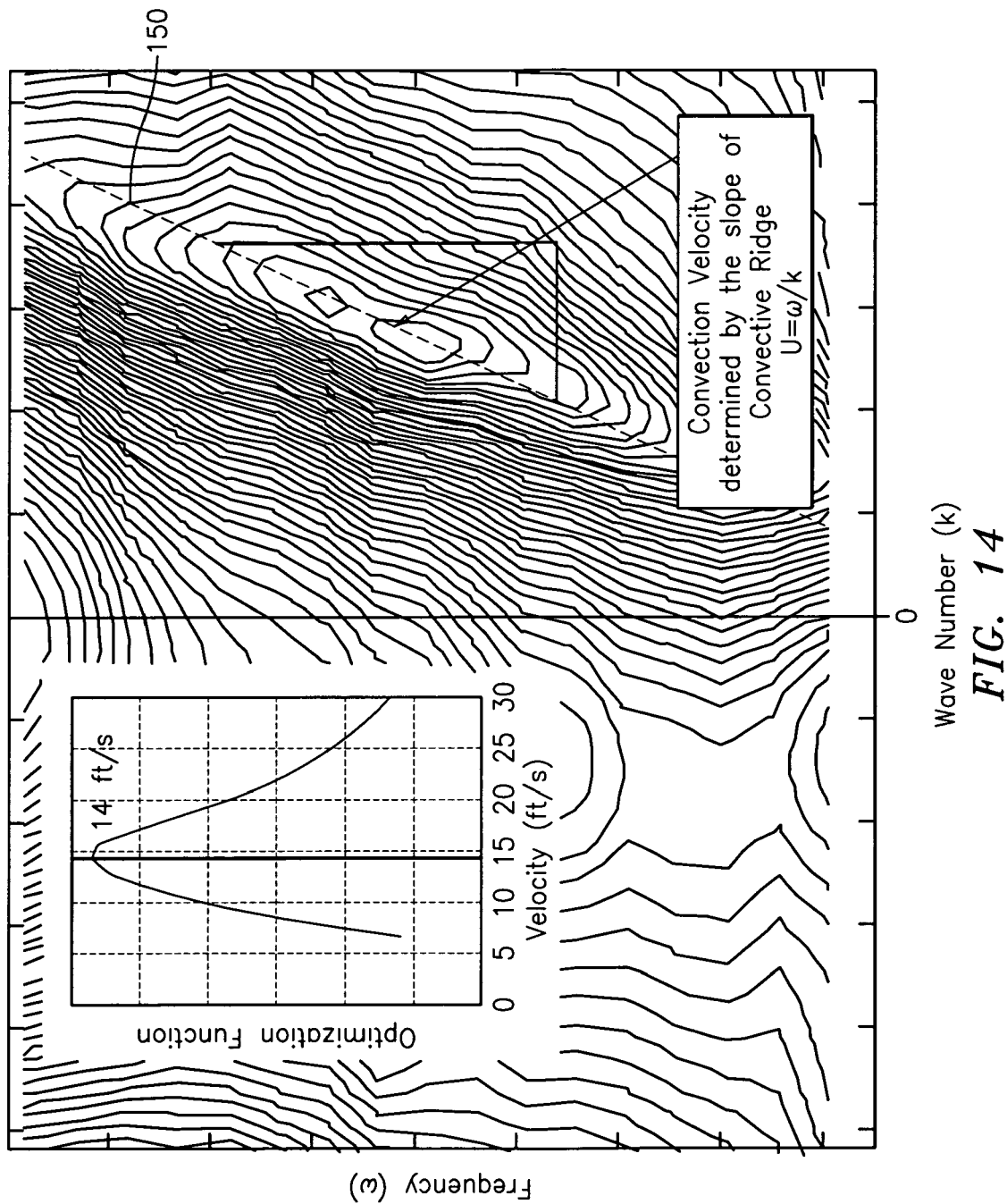
FIG. 14 is a kω plot of data processed from an array of pressure sensors used to measure the velocity of pressure disturbance propagating with the fluid within the submersible meter, in accordance with the present invention.

In the case of suitable turbulent eddies 88 (see FIG. 12) being present, the power in the k-ω plane shown in a k-ω plot of FIG. 14 shows a convective ridge 150. The convective ridge represents the concentration of a stochastic parameter that convects with the fluid and is a mathematical manifestation of the relationship between the spatial variations and temporal variations described above. Such a plot will indicate a tendency for k-ω pairs to appear more or less along a line 100 with some slope, the slope indicating the flow velocity.

Once the power in the k-ω plane is determined, a convective ridge identifier 48 uses one or another feature extraction method to determine the location and orientation (slope) of any convective ridge 150 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 48 provides information about the different trial convection velocities, information referred to generally as convective ridge information.

The analyzer 50 examines the convective ridge information including the convective ridge orientation (slope). Assuming the straight-line dispersion relation given by k=ω/u, the analyzer 50 determines the flow velocity and/or volumetric flow. The volumetric flow is determined by multiplying the cross-sectional area of the inside of the pipe with the velocity of the process flow.

Some or all of the functions within the processing unit 24 may be implemented in software (using a microprocessor or computer) and/or firmware, or may be implemented using analog and/or digital hardware, having sufficient memory, interfaces, and capacity to perform the functions described herein. While the submersible meter 10 is capable of measuring and processing acoustic and vortical disturbance to provide respective outputs, the invention contemplates that the meter may only have either of these functions.

The pressure sensors 18-21 of FIG. 8 described herein may be any type of sensor, capable of measuring the unsteady (or ac or dynamic) pressures or parameter that convects with the flow within the inner pipe 14, such as piezoelectric, optical, capacitive, resistive (e.g., Wheatstone bridge), accelerometers (or geophones), velocity measuring devices, displacement measuring devices, ultra-sonic devices, etc. If optical pressure sensors are used, the sensors 18-21 may be Bragg grating based pressure sensors, such as that described in U.S. Pat. No. 6,016,702, and in U.S. Pat. No. 6,959,604, which are incorporated herein by reference. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

It is also within the scope of the present invention that any strain sensing technique may be used to measure the variations in strain in the pipe, such as highly sensitive piezoelectric, electronic or electric, strain gages and piezo-resistive strain gages attached to the pipe 12. Other strain gages include resistive foil type gages having a race track configuration similar to that disclosed U.S. patent application Ser. No. 09/344,094, filed Jun. 25, 1999, now U.S. Pat. No. 6,354,147, which is incorporated herein by reference. The invention also contemplates strain gages being disposed about a predetermined portion of the circumference of pipe 12. The axial placement of and separation distance $\Delta X_1$, $\Delta X_2$ between the strain sensors are determined as described herein above.

It is also within the scope of the present invention that any other strain sensing technique may be used to measure the variations in strain in the pipe, such as highly sensitive piezoelectric, electronic or electric, strain gages attached to or embedded in the pipe 14.

The submersible meter 10 may include a pressure sensor as shown in FIGS. 3 and 9 for measuring the pressure of the fluid/mixture. Knowing the pressure enables compensation of the gas volume fraction measurement dynamically due to pressure changes of the mixture.

Alternatively, the gas holdup measurement by the meter 10 may be compensated for changes in pressure without having a pressure sensor. The following algorithm provides an iterative process to compensate for pressure fluctuations without having a device for measuring the mixture adjacent to or within the meter. In this embodiment having no pressure sensor or real time measurement of the pressure, the user enters the process pressure into the transmitter at the time of installation. As the gas holdup (GVF) changes in the process, so does the pressure. Under these conditions, the meter's gas holdup measurement will have an offset that is proportional to the pressure change. The following routine may be used to dynamically correct the gas holdup (GVF) reading from the meter for those pressure changes.

The following are the constants and iterative routine variable for the compensation routine that is described in greater detail hereinafter.

| Constants: | | |
|---|---|---|
| $\rho_{air} =$ | lbm/ft³ | (Density of the air at STD conditions) |
| $\rho_{liquid} =$ | lbm/ft³ | (Density of the water at STD conditions) |
| $\rho_{solids} =$ | lbm/ft³ | (Desity of the solids - SG of 3.8) |
| %$_{Solids\ by\ mass} =$ | | (Percent solids by mass - 4.6 g liquid/1 g solid) |
| %$_{Solids\ by\ volume} =$ | | (Percent solids by volume - = (% solids by mass/solid density)/(% solid by mass/solid density + (1-% solid by mass)/liquid density)) |
| $\rho_{non-aerated\ pulp} =$ | lbm/ft³ | (% solid by volume * solids density + % liquid by volume * liquid density |
| Depth$_{sensor} =$ | inches | (Depth measured from the top of the |

-continued

| | | Constants: |
|---|---|---|
| $P_{assumed}$ = | psia | collection zone to the mid point of the sensor) (Assumed pressure as entered in the transmitter) |

| | | Iterative Routine Variables: |
|---|---|---|
| $\epsilon g$ (transmitter) = | % holdup | (4-20 mA output from the transmitter) |
| $P_{iterative}$ = | psia | (First iteration can start with 14.7 psia plus a small increment) |
| $\epsilon g$ (corrected) = | % holdup | $\epsilon g$ (transmitter)*($P_{iteratve}/P_{assumed}$)) |
| $\rho_{aerated\ pulp}$ = | lbm/ft$^3$ | ($\epsilon g$ (corrected)* $\rho$air + (1-$\epsilon g$ (corrected) *$\rho$non-aerated pulp) |
| $P_{corrected}$ = | psia | ((($\rho$air*(Depth$_{sensor}$/12))/144) + 14.7) |
| $P_{iterative\ error}$ = | psi | (iterative pressure difference, the goal is to drive this to zero) |

The iterative compensation algorithm is as follows:
Instructions for Iterative Algorithm
1) Initialize the iterative pressure value to an assumed pressure ($P_{assumed}$)
2) Read in the 4-20 mA gas holdup value from the transmitter of the meter $\epsilon_q$ (transmitter)
3) Increment the iterative pressure value ($P_{iterative}$) by some small increment
4) Correct the gas holdup value from the transmitter $\epsilon_q$ (corrected) with the ratio of the assumed pressure ($P_{assumed}$) and the iterative pressure ($P_{iterative}$)
5) Calculate an aerated pulp density ($\rho_{aerated\ pulp}$) based on the corrected gas holdup $\epsilon_q$ (corrected)
6) Calculate a corrected pressure ($P_{corrected}$) based on the new aerated pulp density ($\rho_{aerated\ pulp}$)
7) Calculate the difference between the interative pressure ($P_{iterative}$) and the corrected pressure ($P_{corrected}$)
8) If the difference (or the iterative pressure error $P_{iterative\ error}$) is greater than 0, then go back to step 3)

Figure 15:
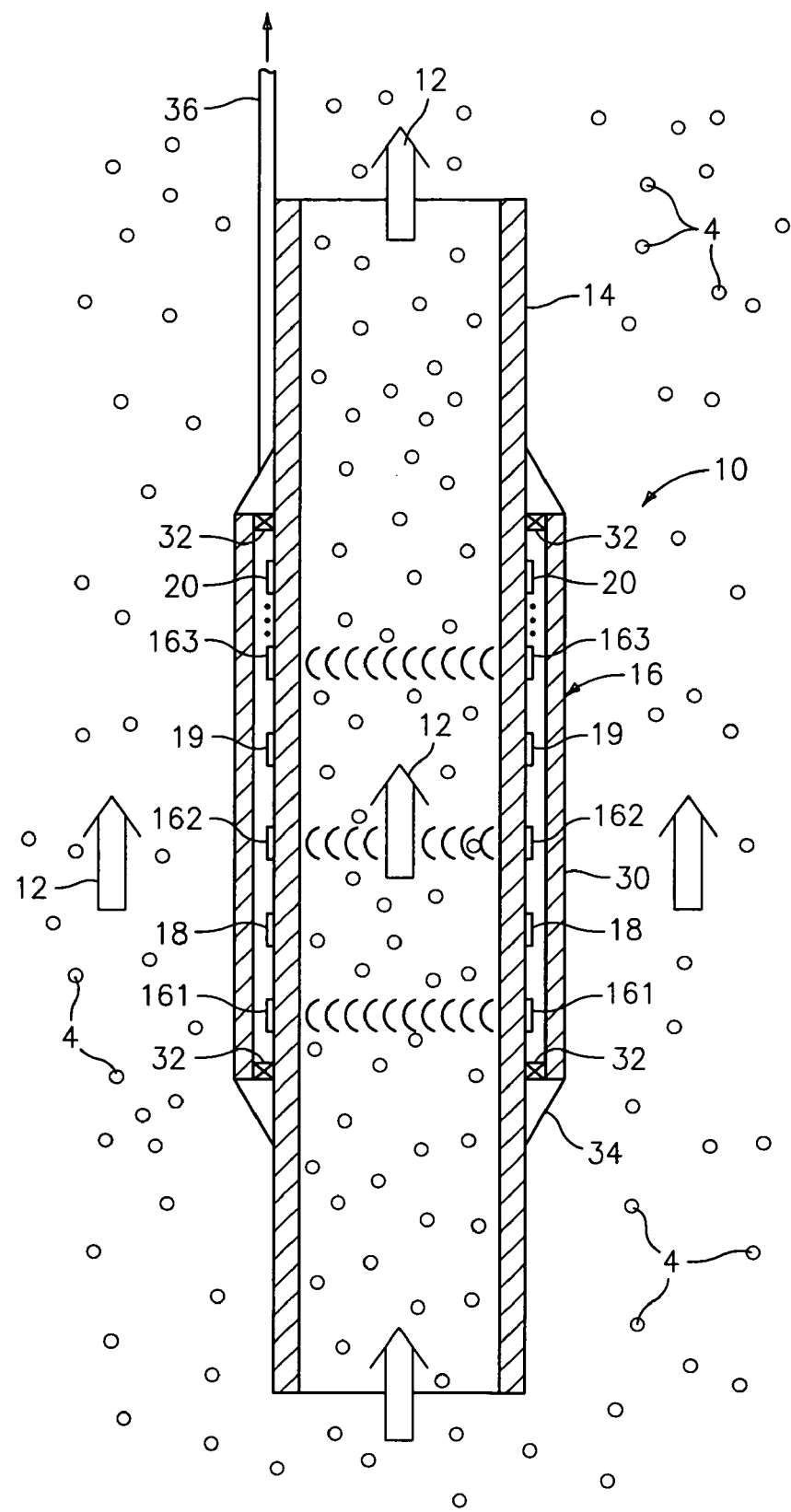
FIG. 15 is a schematic illustration of another embodiment of a submersible meter in accordance with the present invention.

Referring to FIG. 15, the present invention contemplates that the sensor portion 16 includes both an array of pressure sensors 18-20 as described hereinbefore to measure the acoustic pressures within the inner pipe 14 to determine the gas holdup of the aerated fluid, and an array of ultrasonic sensors 161-163 (having a transmitter and a receiver) to measure the flow rate. The ultrasonic sensor array may measure the attenuation and/or time of flight of the ultrasonic signal at each location wherein the transmitter 24 processes the data similar to that described hereinbefore. This ultrasonic sensor array or meter is similar to that described in U.S. Patent Application Ser. No. 60/510,218 and U.S. patent application Ser. No. 10/756,977, which are incorporated herein by reference.

Figure 16:
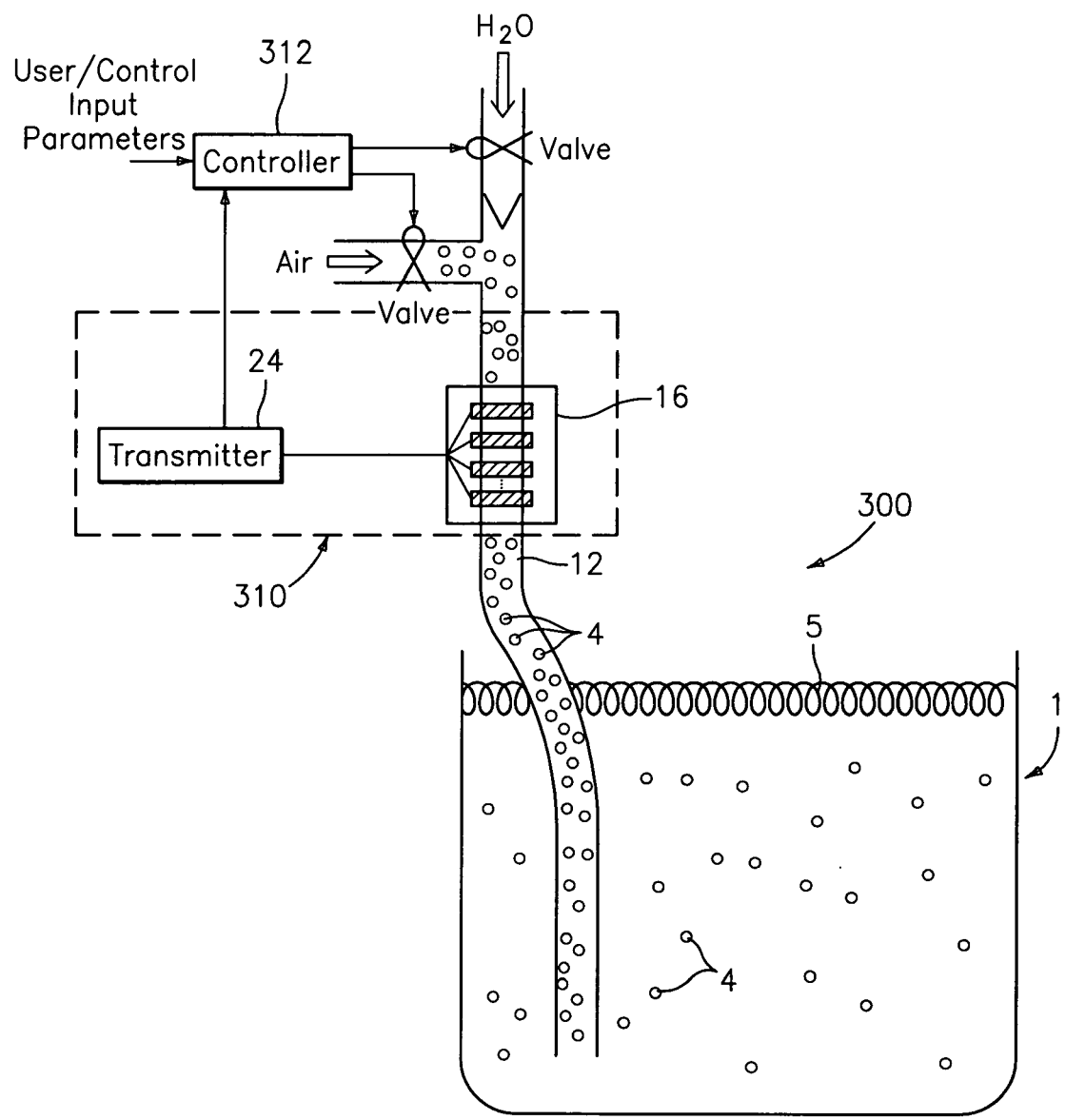
FIG. 16 is a schematic diagram of a closed loop control system of an external sparger for mineral processing embodying the present invention.

FIG. 16 illustrates an external sparger 300 wherein the bubbles 4 are created by drawing air into water or other fluid, which is then provided to the flotation tank 1/column cell 6. The present invention contemplates a meter 310 mounted to the pipe having the aerated water or fluid to determine the gas volume fraction of the fluid/mixture 12 to provide information to correlate the efficient of the separation of the ore. The meter is similar to that described in U.S. Pat. No. 6,354,147, U.S. Pat. No. 6,587,798, U.S. Pat. No. 7,062,973, U.S. patent application Ser. No. 10/712,818, and U.S. patent application Ser. No. 10/712,833.

The meter 310 may also be used to close a control loop in the operation of the external sparger 300. For example, measure signal provided by the meter may be provided to a controller 312. In response to the measured signal and a user input or control parameter, the controller may provide a control signal to a valve that controls the amount of air in the aerated water (or fluid) and/or a control signal to a valve that controls the amount of water (or fluid) in the aerated fluid added to the flotation tank 1.

While the description has described the apparatus as two separate meters that measure the vortical disturbances and the speed of sound, respectively, as suggested by FIG. 3, the processing could function as two separate meters, a combination (simultaneous operation) of both function, or selectively chose between operations, similar to that described in U.S. Pat. No. 7,127,360, and U.S. Pat. No. 7,295,933, which are incorporated herein by reference.

While the housing is should to have a circular or square cross-sectional shape, the present invention contemplates that the cross-sectional shape may be any generally polygonal, oval, triangular and rectangular shape.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. A control system for controlling the processing of an aerated fluid comprising:
   a submersible meter adapted to be disposed in the aerated fluid for measuring at least one parameter of the fluid; said submersible meter including:
      a tube submersible within the aerated fluid having an open input end and an open output end for receiving only a portion of the aerated fluid;
      an array of sensors, each sensor being disposed at different axial locations along the tube and measuring at a corresponding axial location an acoustic pressure propagating axially through the aerated fluid in the tube, each sensor providing a measured signal indicative of the acoustic pressure at said corresponding axial location;
      a signal processor, responsive to said measured signals, which outputs at least a gas holdup of the aerated fluid, and
      wherein the signal processor determines the gas holdup using an array processing algorithm; and
   a control device receiving said gas holdup and controlling the at least one process parameter to a desired level.

2. The control system of claim 1, wherein the measured signals are indicative of passive acoustic noise propagating through the aerated fluid within the tube.

3. The control system of claim 1, wherein the signal processor, responsive to said measured signals, provides a speed of sound propagating axially through the aerated fluid.

4. The control system of claim 1, wherein the array comprises 5, 6, 7, 8, 9, 10, 11, 12, 13, 14, 15, or 16 sensors.

5. The control system of claim 1, wherein at least one of said sensors include a pressure sensor, a displacement sensor, or a strain-based sensor.

6. The control system of claim 1, wherein the signal processor, responsive to the measured signals, outputs a bubble size ($d_b$) of the bubbles of the aerated fluid.

7. The control system of claim 6, wherein the signal processor determines the bubble size ($d_b$) using a drift flux analysis method.

8. The control system of claim 1, wherein the array of sensors are spaced sufficiently apart such that the entire length of the array is at least a significant fraction of the measured wavelength of acoustic waves being measured to determine a speed of sound propagating axially through the aerated fluid in the tube.

9. The control system of claim 1, wherein the aerated fluid includes at least a solid material and/or at least one liquid.

10. The control system of claim 1, wherein the signal processor determines the slope of an acoustic ridge in a k-ω plane to determine the speed of sound propagating axially through the aerated fluid flowing through the tube.

11. A control system for controlling the process of mineral processing; said control system comprising:
a submersible meter including:
a tube submersible within an aerated fluid having an open input end and an open output end for receiving only a portion of the aerated fluid;
an array of sensors, each sensor being disposed at different axial locations along the tube and measuring at a corresponding axial location an acoustic pressure propagating axially through the aerated fluid in the tube, each sensor providing a measured signal indicative of the acoustic pressure at said corresponding axial location; and
a signal processor, responsive to said measured signals, which outputs at least a gas holdup of the aerated fluid; and
a control device receiving said gas holdup and controlling at least one process parameter to a desired level.

12. The control system of claim 11, wherein the measured signals are indicative of passive acoustic noise propagating through the aerated fluid within the tube.

13. The control system of claim 11, wherein the control device includes at least one of a pump, valve, or throttle.

14. The control system of claim 11, wherein the at least one process parameter includes a bubble size ($d_b$).

15. The control system of claim 14, wherein the signal processor determines the bubble size ($d_b$) using a drift flux analysis method.

16. The control system of claim 11, wherein the signal processor determines at least one of a bubble size ($d_b$).

17. The control system of claim 11, wherein the signal processor, responsive to said measured signals, provides speed of sound propagating axially through the aerated fluid.

18. The control system of claim 11, wherein the array comprises 5, 6, 7, 8, 9, 10, 11, 12, 13, 14, 15, or 16 strain sensors.

19. The control system of claim 11, wherein at least one of said sensors include a pressure sensor, a displacement sensor, or a strain based sensor.

20. The control system of claim 1, wherein the signal processor determines the slope of an acoustic ridge in a k-ω plane to determine the speed of sound propagating axially through the aerated fluid flowing through the tube.

21. The control system of claim 11, wherein the array of sensors measures the acoustic pressure of a one-dimensional acoustic wave propagating axially through the aerated fluid within the tube.

22. The control system of claim 11, further includes an acoustic source that provides the acoustic pressure propagating axially through the aerated fluid within the tube.

23. The control system of claim 11, wherein the array comprises two sensors.

24. The control system of claim 11, wherein the array comprises three sensors.

25. The control system of claim 11, wherein the array comprises four sensors.

26. The control system of claim 11, wherein the signal processor, responsive to the measured signals, outputs a flotation rate constant (k).

27. The control system of claim 11, wherein the signal processor, responsive to the measured signals, outputs a bubble surface areas flux ($S_b$).

28. The control system of claim 11, wherein the signal processor determines the gas holdup using an array processing algorithm.

29. The control system of claim 11, wherein the signal processor outputs the gas holdup using an array processing algorithm.

30. The control system of claim 11, wherein the signal processor, responsive to the measured signals, provides an output indicative of the velocity of the aerated fluid flowing through the tube.

31. The control system of claim 30, wherein the signal processor determines the slope of a convective ridge in k-ω plane to determine the velocity of the aerated fluid through the tube.

32. The control system of claim 30, wherein the signal processor determines the velocity using an array processing algorithm.

33. A control system for controlling the process of mineral processing; said control system comprising:
a submersible meter including:
a tube submersible within an aerated fluid having an open input end and an open output end for receiving only a portion of the aerated fluid;
a first array of sensors, each sensor being disposed at different axial locations along the tube and measuring at a corresponding axial location an acoustic pressure propagating axially through the aerated fluid in the tube, each sensor providing a first measured signal indicative of the acoustic pressure at said corresponding axial location;
a second array comprising at least two ultrasonic sensors, each ultrasonic sensor being disposed at different axial locations along the tube, and each ultrasonic sensor measuring a characteristic of the aerated fluid at a corresponding axial location, each ultrasonic sensor providing a second measured signal indicative of the characteristic at said corresponding axial location of each ultrasonic sensor; a signal processor, responsive to said measured signals, which outputs at least a gas holdup of the aerated fluid; and
a control device receiving said gas holdup and controlling at least one process parameter to a desired level;
wherein the signal processor, responsive to said second measured signals, outputs a velocity of the aerated fluid flowing through the tube.

34. The control system of claim 33, wherein the second array comprises at least 3, 4, 5, 6, 7, 8, 9, 10, 11, 12, 13, 14, 15, or 16 ultrasonic sensors.

35. The control system of claim 34, wherein the signal processor, responsive to the measured signals, determines the slope of a convective ridge in k-ω plane to output the velocity of the aerated fluid flowing through the tube.

36. The control system of claim 34, wherein the signal processor determines the velocity using an array processing algorithm.

37. The control system of claim 11, wherein the aerated fluid comprises a liquid having entrained gaseous bubbles.

38. The control system of claim 1, wherein the array of sensors measures the acoustic pressure of a one-dimensional acoustic wave propagating axially through the aerated fluid within the tube.

39. The control system of claim 1, further includes an acoustic source that provides the acoustic pressure propagating axially through the aerated fluid within the tube.

40. The control system of claim 1, wherein the array comprises two sensors.

41. The control system of claim 1, wherein the array comprises three sensors.

42. The control system of claim 1, wherein the array comprises four sensors.

43. The control system of claim 1, wherein the signal processor, responsive to the measured signals, outputs a flotation rate constant (k).

44. The control system of claim 1, wherein the signal processor, responsive to the measured signals, outputs a bubble surface areas flux ($S_b$).

45. The control system of claim 1, wherein the signal processor, responsive to the measured signals, provides an output indicative of the velocity of the aerated fluid flowing through the tube.

46. The control system of claim 45, wherein the signal processor determines the slope of a convective ridge in k-$\omega$ plane to determine the velocity of the aerated fluid through the tube.

47. The control system of claim 45, wherein the signal processor determines the velocity using an array processing algorithm.

* * * * *